US009096653B2

(12) United States Patent
Schneerson et al.

(10) Patent No.: US 9,096,653 B2
(45) Date of Patent: Aug. 4, 2015

(54) MULTICOMPONENT VACCINE FOR MALARIA PROVIDING LONG-LASTING IMMUNE RESPONSES AGAINST PLASMODIA

(71) Applicants: The United States of America, as represented by the Secretary, Department of Health and Human Services, Washington, DC (US); New York University, New York, NY (US)

(72) Inventors: Rachel Schneerson, Bethesda, MD (US); Joanna Kubler-Kielb, Bethesda, MD (US); John B. Robbins, New York, NY (US); Fathy Majadly, Frederick, MD (US); Christopher P. Mocca, Columbia, MD (US); Jerry Keith, Olney, MD (US); Zuzana Biesova, Rockville, MD (US); Louis Miller, Cabin John, MD (US); Ruth Nussenzweig, New York, NY (US); Darrell T. Liu, Bethesda, MD (US)

(73) Assignees: The United States of America, as represented by the Secretary, Department of Health and Human Services, Washington, DC (US); New York University, New York, NY (US)

( * ) Notice: Subject to any disclaimer, the term of this patent is extended or adjusted under 35 U.S.C. 154(b) by 21 days.

(21) Appl. No.: 13/870,547

(22) Filed: Apr. 25, 2013

(65) Prior Publication Data
US 2013/0216570 A1    Aug. 22, 2013

Related U.S. Application Data

(62) Division of application No. 13/121,574, filed as application No. PCT/US2009/059284 on Oct. 1, 2009, now Pat. No. 8,444,996.

(60) Provisional application No. 61/101,944, filed on Oct. 1, 2008, provisional application No. 61/112,572, filed on Nov. 7, 2008.

(51) Int. Cl.
*A61K 39/385*  (2006.01)
*A61K 39/015*  (2006.01)
*C07K 14/00*   (2006.01)
*A61K 47/48*   (2006.01)

(52) U.S. Cl.
CPC .............. *C07K 14/00* (2013.01); *A61K 39/015* (2013.01); *A61K 47/4833* (2013.01)

(58) Field of Classification Search
CPC ... A61K 39/015; A61K 47/4833; C07K 14/00
USPC ..................... 424/193.1, 194.1, 265.1, 272.1; 530/350, 363, 367
See application file for complete search history.

(56) References Cited

U.S. PATENT DOCUMENTS

| | | | |
|---|---|---|---|
| 5,614,194 | A | 3/1997 | Colman et al. |
| 5,766,597 | A | 6/1998 | Paoletti et al. |
| 5,853,739 | A | 12/1998 | Kaslow et al. |
| 5,928,902 | A | 7/1999 | De Wilde et al. |
| 6,669,945 | B1 | 12/2003 | Nardin et al. |
| 8,444,996 | B2 * | 5/2013 | Schneerson et al. ....... 424/193.1 |
| 2004/0176283 | A1 | 9/2004 | Robinson et al. |
| 2005/0249750 | A1 | 11/2005 | Nardin et al. |
| 2010/0183678 | A1 | 7/2010 | Schneerson et al. |

FOREIGN PATENT DOCUMENTS

| | | |
|---|---|---|
| WO | WO 99/029868 | 6/1999 |
| WO | WO 2006/124712 | 11/2006 |
| WO | WO 2008/048945 | 4/2008 |

OTHER PUBLICATIONS

Le et al Vaccine, vol. 16, No. 2/3, pp. 305-312, 1998.*
Udhayakumar Vaccine, vol. 16, No. 9110. pp. 982-988, 1998.*
Dame et al., "Structure of the Gene Encoding the Immunodominant Surface Antigen on the Sporozoite of the Human Malaria Parasite *Plasmodium falciuparum*," *Science*, vol. 225, pp. 593-599, 1984.
Duffy et al., "A Novel Malaria Protein, Pfs28, and Pfs25 Are Genetically Linked and Synergistic as Falciparum Malaria Transmission-Blocking Vaccines," *Infection and Immunity*, Vo. 65, No. 3, pp. 1109-1113, 1997.
Gerloff et al., "Structural models for the protein family characterized by gamete surface protein Pfs230 of *Plasmodium falciparum*," *Proc. Natl. Acad. Sci. USA*, vol. 102, No. 38, pp. 13598-13603, 2005.
Healer et al., "Complement-Mediated Lysis of *Plasmodium falciparum* Gametes by Malaria-Immune Human Sera is Associated with Antibodies to the Gamete Surface Antigen Pfs230," *Infection and Immunity*, vol. 65, No. 8, pp. 3017-3023, 1997.
Kubler-Kielb et al., "Additional Conjugation Methods and Immunogenicity of *Bacillus anthracis* Poly-γ-D-Glutamic Acid-Protein Conjugates," *Infection and Immunity*, vol. 74, No. 8, pp. 4744-4749, 2006.
Kubler-Kielb et al., "Long-lasting and transmission-blocking activity of antibodies to *Plasmodium falciparum* elicited in mice by protein conjugates of Pfs25," *Proc. Natl. Acad. Sci. USA*, vol. 104, No. 1, pp. 293-298, 2007.
Outchkourov et al., "Correctly folded Pfs48/45 protein of *Plasmodium falciparum* elicits malaria transmission-blocking immunity in mice," *Proc. Natl. Acad. Sci. USA*, vol. 105, No. 11, pp. 4301-4305, 2008.

(Continued)

*Primary Examiner* — Padma V Baskar
(74) *Attorney, Agent, or Firm* — Klarquist Sparkman, LLP

(57) ABSTRACT

Disclosed are immunogenic conjugates which elicit an immune response to *Plasmodium* proteins. In particular examples, the *Plasmodium* proteins include sexual stage surface proteins, circumsporozoite protein (CSP), or immunogenic portions of CSP. Also provided herein are immunogenic compositions including one or more of the disclosed immunogenic conjugates and a pharmaceutically acceptable carrier. Further provided is a method of eliciting an immune response to *Plasmodium* in a subject, comprising administering to the subject an immunogenic composition disclosed herein.

12 Claims, 3 Drawing Sheets

(56) References Cited

OTHER PUBLICATIONS

Schneerson, "Peptide-Protein Conjugate Vaccines," National Institute of Child Health and Human Development Annual Report, 2007 (3 pages).

Wilson et al., "Recognition of phage-expressed peptides containing Asx-Pro sequences by monoclonal antibodies produced against *Plasmodium falciparum* circumsporozoite protein," *Protein Eng.*, vol. 10, No. 5, pp. 531-540, 1997.

Zavala et al., "Rationale for Development of a Synthetic Vaccine Against *Plasmodium falciparum* Malaria," *Science*, vol. 228, pp. 1436-1440, 1985.

Arakawa et al., "Nasal Immunization with a Malaria Transmission-Blocking Vaccine Candidate, Pfs25, Induces Complete Protective Immunity in Mice against Field Isolates of *Plasmodium falciparum*," *Infection and Immunity*, vol. 73, No. 11 pp. 7375-7380, 2005.

Yang et al, "Induction of Protective Antibodies in *Saimiri* Monkeys by Immunization with a Multiple Antigen Construct (MAC) Containing the *Plasmodium vivax* Circumsporozoite Protein Repeat Region and a Universal T Helper Epitope of Tetanus Toxin," *Vaccine*, vol. 15, No. 4, pp. 377-386, 1997.

\* cited by examiner

FIG. 1B

Pr- Pfs/Pfs or BSA
n = 4 or 5

MULTICOMPONENT VACCINE FOR MALARIA PROVIDING LONG-LASTING IMMUNE RESPONSES AGAINST PLASMODIA

CROSS REFERENCE TO RELATED APPLICATIONS

This is a divisional of U.S. patent application Ser. No. 13/121,574, filed Mar. 29, 2011, now U.S. Pat. No. 8,444,996, issued May 21, 2013, which is the §371 U.S. National Stage of International Application No. PCT/US2009/059284, filed Oct. 1, 2009, which was published in English under PCT Article 21(2), which in turn claims the benefit of U.S. Provisional Application No. 61/101,944, filed Oct. 1, 2008, and U.S. Provisional Application No. 61/112,572, filed Nov. 7, 2008, all of which are incorporated herein in their entirety.

FIELD

Immunogenic conjugates are disclosed for use in eliciting an immune response to *Plasmodium* in a subject and protecting subjects from infection with *Plasmodium*.

BACKGROUND

Malaria ranks as one of the world's top three deadliest diseases (approximately 300 million cases per year). *P. falciparum* causes the most severe form, causing the death of about 1 million people annually (90 percent of whom are young children).

Infection begins when malaria sporozoites are injected into the bloodstream of a host by a mosquito. After injection, they migrate to the liver and multiply in hepatocytes for one to two weeks. The sporozoites differentiate to merozoites which are released from the liver into the blood stream, where they infect erythrocytes. When the merozoite matures in the red blood cell, it is known as a trophozoite and, when fully developed, as a schizont. A schizont is the stage when nuclear division occurs to form individual merozoites which are released to invade other red cells. After several schizogonic cycles, some parasites, instead of becoming schizonts through asexual reproduction, develop into large uninucleate parasites. These parasites undergo sexual development.

Sexual development of the malaria parasites involves the female macrogametocyte and the male microgametocyte. If a mosquito feeds on the blood of an infected host, it can ingest gametocytes within the blood. Fertilization and sexual recombination of the parasite occurs in the mosquito's gut. The fertilized parasite, which is known as a zygote, then develops into an ookinete. The ookinete penetrates the midgut wall of the mosquito and develops into an oocyst, within which many small sporozoites form. When the oocyst ruptures, the sporozoites migrate to the salivary gland of the mosquito via the hemolymph. Once in the saliva of the mosquito, the parasite can be injected into a host, repeating the life cycle.

There is no vaccine, and malarial parasites are increasingly becoming resistant to antimalarial drugs that have been used to treat the disease for decades.

SUMMARY

Disclosed are immunogenic conjugates which elicit an immune response to *Plasmodium* proteins. In particular examples, the *Plasmodium* proteins include sexual stage surface proteins (such as P25, P28, P48/45, or P230), asexual circumsporozoite protein (CSP), or immunogenic portions thereof. Provided herein are immunogenic conjugates that include at least one *Plasmodium* sexual stage surface protein (for example, P25, P28, P48/45, or P230) covalently linked to at least one *Plasmodium* circumsporozoite protein (CSP) or an immunogenic portion of CSP. The proteins or peptides are covalently linked, such as by a non-peptide linker (such as an amide linkage, a hydrazone linkage, or a thioether linkage) or by a peptide linker (such as about one to twelve peptide bonds). In particular examples, the immunogenic conjugates include at least one sexual stage surface protein Pfs25 or Pvs25 (for example, at least one, two, three, four, or five Pfs25 or Pvs25 proteins) covalently linked to at least one CSP. In additional examples, the immunogenic conjugates include at least one sexual stage surface protein (such as P25, P28, P48/45, or P230) covalently linked to at least one immunogenic repeat derived from a *Plasmodium* CSP, for example, at least one Asn-Ala-Asn-Pro (NANP) (SEQ ID NO: 1) repeat, at least one Asn-Pro-Asn-Ala (NPNA) (SEQ ID NO: 2) repeat, at least one Pro-Asn-Ala-Asn (PNAN) (SEQ ID NO: 3) repeat, at least one Ala-Asn-Pro-Asn (ANPN) (SEQ ID NO: 4) repeat, or a combination of two or more thereof.

Also provided are immunogenic conjugates that include a peptide having at least one immunogenic repeat derived from a *Plasmodium* CSP, for example, at least one NPNA (SEQ ID NO: 2) repeat, at least one PNAN (SEQ ID NO: 3) repeat, or at least one ANPN (SEQ ID NO: 4) repeat covalently linked to at least one other immunogenic protein (such as an immunogenic protein other than a *Plasmodium* protein, such as a protein that elicits an immune response, for example, a bacterial toxin). The proteins or peptides are covalently linked, such as by a non-peptide linker (such as an amide linkage, a hydrazone linkage, or a thioether linkage) or by a peptide linker (such as about one to twelve peptide bonds or amino acids).

Further provided are immunogenic conjugates including a peptide having a *Plasmodium* T-cell epitope (such as a T-cell epitope from CSP) and at least four CSP immunogenic repeats (for example, NANP (SEQ ID NO: 1), NPNA (SEQ ID NO: 2), PNAN (SEQ ID NO: 3), or ANPN (SEQ ID NO: 4) repeats) covalently linked to at least one other immunogenic protein (such as an immunogenic protein other than a *Plasmodium* protein, such as a human pathogen protein that elicits an immune response, such as a bacterial toxin). The proteins are covalently linked, such as by a non-peptide linker (such as an amide linkage, a hydrazone linkage, or a thioether linkage) or by a peptide linker (such as about one to twelve peptide bonds).

Also provided herein are immunogenic compositions including one or more of the disclosed immunogenic conjugates and a pharmaceutically acceptable carrier. Further provided is a method of eliciting an immune response to *Plasmodium* (for example *P. falciparum, P. vivax, P. ovale, P. malariae*, or *P. knowlesi*), such as an immune response to both sexual and asexual stages of *Plasmodium* or to a *Plasmodium* CSP or portion thereof in a host (such as a host in need of enhanced immunity to *Plasmodium*), including administering to the host an immunogenic composition disclosed herein.

The foregoing and other features of the disclosure will become more apparent from the following detailed description, which proceeds with reference to the accompanying figures.

BRIEF DESCRIPTION OF THE DRAWINGS

FIG. 1B is a diagram showing the two-step procedure for preparing Pfs25-Pfs25 protein conjugates.

SEQUENCE LISTING

Figure 1A:
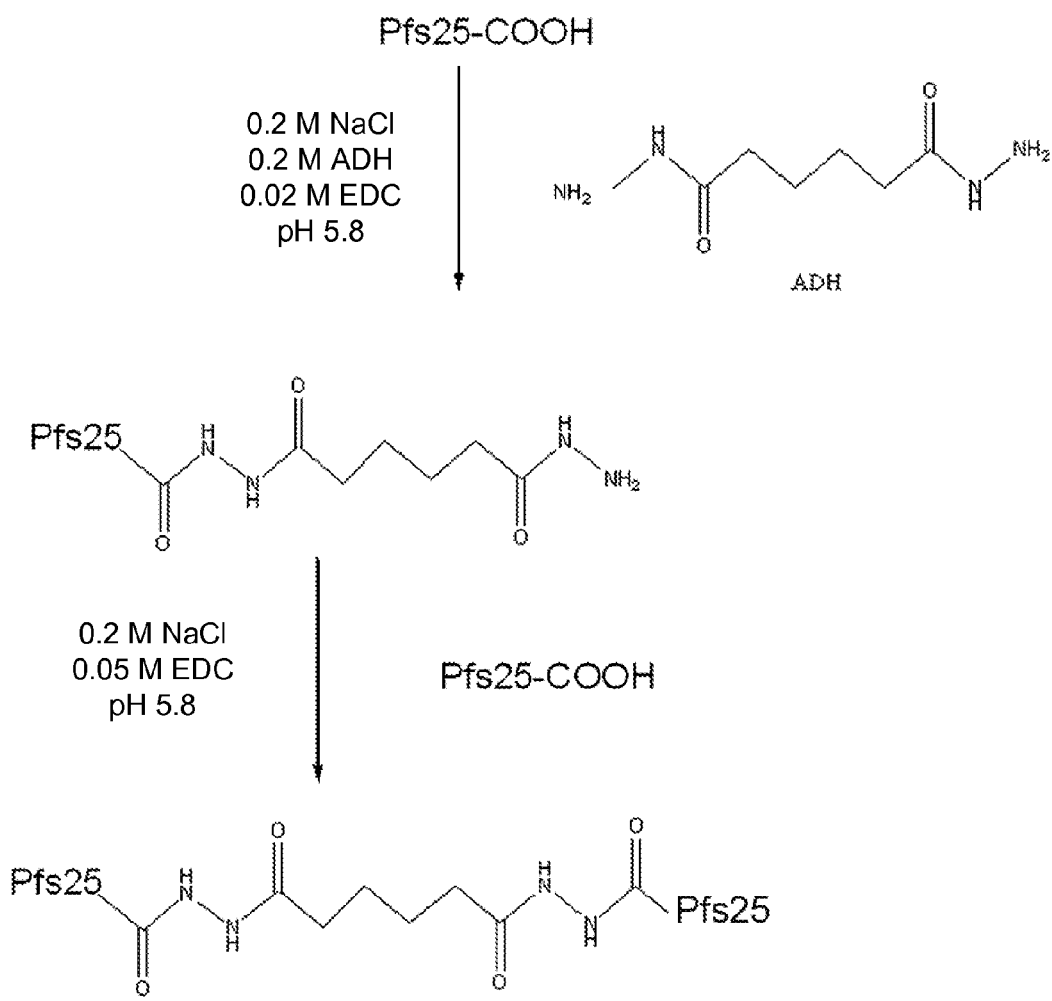
FIG. 1A is a diagram showing the one-step procedure for preparing Pfs25-Pfs25 protein conjugates.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

The Sequence Listing is submitted as an ASCII text file in the form of the file named Sequence_Listing.txt, which was created on Apr. 23, 2013, and is 16,698 bytes, which is incorporated by reference herein.

SEQ ID NO: 1 is the amino acid sequence NANP.
SEQ ID NO: 2 is the amino acid sequence NPNA.
SEQ ID NO: 3 is the amino acid sequence PNAN.
SEQ ID NO: 4 is the amino acid sequence ANPN.
SEQ ID NOs: 5 and 6 are the nucleic acid and amino acid sequences, respectively, of an exemplary *P. falciparum* CSP protein, modified to remove the GPI anchor and to add a C-terminal 6×His tag for purification.
SEQ ID NO: 7 is the amino acid sequence of an exemplary *P. falciparum* Pfs25 protein.
SEQ ID NO: 8 is the amino acid sequence of an exemplary *P. vivax* Pvs25 protein.
SEQ ID NO: 9 is the amino acid sequence of a *P. vivax* VK210 CSP repeat.
SEQ ID NO: 10 is the amino acid sequence of a *P. vivax* VK247 CSP repeat.
SEQ ID NO: 11 is the amino acid sequence of a *P. malariae* CSP repeat.
SEQ ID NO: 12 is the amino acid sequence of a *P. knowlesi* CSP repeat.
SEQ ID NO: 13 is the amino acid sequence of a *P. ovale* CSP repeat.
SEQ ID NO: 14 is the amino acid sequence of a universal T cell epitope from *P. falciparum* CSP.
SEQ ID NO: 15 is the amino acid sequence of a T cell epitope from *P. falciparum* CSP.
SEQ ID NO: 16 is the amino acid sequence of a peptide of four NANP repeats.
SEQ ID NO: 17 is the amino acid sequence of a peptide of five NANP repeats.
SEQ ID NO: 18 is the amino acid sequence of a peptide of four NPNA repeats.
SEQ ID NO: 19 is the amino acid sequence of a peptide of five NPNA repeats.
SEQ ID NO: 20 is the amino acid sequence of a peptide of four PNAN repeats.
SEQ ID NO: 21 is the amino acid sequence of a peptide of five PNAN repeats.
SEQ ID NO: 22 is the amino acid sequence of a peptide of four ANPN repeats.
SEQ ID NO: 23 is the amino acid sequence of a peptide of five ANPN repeats.
SEQ ID NO: 24 is the amino acid sequence of a peptide of six NANP repeats.
SEQ ID NO: 25 is the amino acid sequence of a peptide having four NANP repeats conjugated to a universal T cell epitope from *P. falciparum* CSP.
SEQ ID NO: 26 is the amino acid sequence of a peptide having five NANP repeats conjugated to a universal T cell epitope from *P. falciparum* CSP.
SEQ ID NO: 27 is the amino acid sequence of a peptide having four ANPN repeats conjugated to a universal T cell epitope from *P. falciparum* CSP.
SEQ ID NO: 28 is the amino acid sequence of a peptide having five ANPN repeats conjugated to a universal T cell epitope from *P. falciparum* CSP.
SEQ ID NO: 29 is the amino acid sequence of a peptide having four NPNA repeats conjugated to a universal T cell epitope from *P. falciparum* CSP.
SEQ ID NO: 30 is the amino acid sequence of a peptide having five NPNA repeats conjugated to a universal T cell epitope from *P. falciparum* CSP.
SEQ ID NO: 31 is the amino acid sequence of a peptide having four PNAN repeats conjugated to a universal T cell epitope from *P. falciparum* CSP.
SEQ ID NO: 32 is the amino acid sequence of a peptide having five PNAN repeats conjugated to a universal T cell epitope from *P. falciparum* CSP.

DETAILED DESCRIPTION

I. Abbreviations
ADH: adipic acid dihydrazide
BSA: bovine serum albumin
CSP: circumsporozoite protein
EDC: 1-ethyl-3-[3-dimethylaminopropyl]carbodiimide hydrochloride
ELISA: enzyme-linked immunosorbent assay
IFA: immunofluorescence assay
Pfs25: *Plasmodium falciparum* ookinete surface protein 25
Pvs25: *Plasmodium vivax* ookinete surface protein 25
SBAP: N-succinimidyl-3-bromoacetamidopropionate
SFB: N-succinimidyl-4-formylbenzoate
SPDP: N-succinimidyl-3-(2-pyridyldithio)-propionate II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (such as alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In one embodiment, an antigen is a *Plasmodium* antigen (such as a *Plasmodium* sexual stage surface protein, CSP, or an immunogenic portion thereof).

Circumsporozoite protein (CSP): The circumsporozoite protein (CSP) is a major malaria parasite surface protein during the sporogonic cycle. CSP covers the surface of *Plasmodium* sporozoites, which are transmitted from the mosquito salivary gland to host hepatocytes. It is highly immunogenic, and in endemic areas high antibody titers against this protein are observed in circulating blood. See, e.g., Dame et al., *Science* 225:593-599, 1985; Zavala et al., *Science* 228:1436-1440, 1985; International Publication No. WO 2008/107370.

CSP sequences are publicly available. For example, GenBank accession number NC_000521.3 (incorporated herein by reference on Nov. 7, 2008) discloses a CSP gene from *P. falciparum* 3D7. GenBank accession numbers XM_001351086.1 and XP_001351122.1 (incorporated herein by reference on Nov. 7, 2008) disclose *P. falciparum* 3D7 CSP cDNA and protein sequences respectively. In one example, CSP is the *P. falciparum* CSP nucleic acid and protein sequence shown in SEQ ID NOs: 5 and 6 respectively. Orthologs of CSP are present in other *Plasmodium* species (such as *P. vivax, P. ovale, P. malariae*, and *P. knowlesi*) and are known to those of skill in the art.

Conjugate: A compound formed by joining two or more compounds (such as two or more proteins or fragments of proteins, for example, two or more immunogenic proteins, immunogenic fragments of proteins, or combinations thereof). The conjugates described herein are formed by covalently joining two or more proteins or immunogenic fragments thereof (for example, immunogenic peptides). In some examples, the proteins or peptides are joined by a non-peptide linker, such as a hydrazone linker, an amide linker, a thioether linker, or combinations of two or more thereof. In other examples, the proteins or peptides are joined by a peptide linker, such as a linker including about one to twelve peptide bonds.

Host: A cell or organism which harbors another organism or biological entity, usually a parasite (such as a malaria parasite). In one example, a host is a human or non-human primate that can be or is infected by the malaria parasite *Plasmodium* (such as *P. falciparum, P. vivax, P. ovale, P. malariae*, or *P. knowlesi*). The term "host" is used interchangeably with the term "subject" herein.

Immune response: A response of a cell of the immune system, such as a B-cell, T-cell, macrophage or polymorphonucleocyte, to a stimulus such as an antigen. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection).

Immunogen: A compound, composition, or substance which is capable, under appropriate conditions, of stimulating an immune response, such as the production of antibodies or a T-cell response in an animal, including compositions that are injected or absorbed into an animal. As used herein, an "immunogenic composition" is a composition comprising an immunogen.

Immunize: To render a subject protected from an infectious disease, such as by vaccination.

Isolated: An "isolated" biological component (such as a nucleic acid, protein or pathogen) has been substantially separated or purified away from other biological components (such as cell debris, or other proteins or nucleic acids). Biological components that have been "isolated" include those components purified by standard purification methods. The term also embraces recombinant nucleic acids, proteins or pathogens, as well as chemically synthesized nucleic acids or peptides.

Malaria: Malaria is a parasitic infection of humans and non-human primates by the *Plasmodium* species *P. falciparum, P. vivax, P. ovale, P. malariae*, and *P. knowlesi*. Humans become infected following the bite of an infected anopheline mosquito, the host of the malarial parasite. Malaria occasionally occurs in humans following a blood transfusion or subsequent to needle-sharing. Clinical manifestations of malarial infection which may occur include blackwater fever, cerebral malaria, respiratory failure, hepatic necrosis, and occlusion of myocardial capillaries. Additional *Plasmodium* species infect other hosts, such as rodents (*P. berghei, P. chabaudi, P. vinckei*, and *P. yoelii*), other mammals, birds, and reptiles.

P25: A family of cysteine-rich 25 kDa antigens that includes *Plasmodium falciparum* mosquito stage antigen Pfs25 and its ortholog in *Plasmodium vivax*, Pvs25 (see Kaslow et al., *Nature* 333:74-76, 1988; Malkin et al., *Vaccine* 23:3131-3138, 2005). P25 proteins are composed of four tandem epidermal growth factor-like domains and are expressed on zygotes and mature ookinete stages of parasites within mosquitoes. Because P25 is only expressed in the mosquito midgut and not in the vertebrate host, these proteins have not been under selection pressure by the host immune system and antigenic variation of P25 appears to be more limited than most vaccine candidates present in asexual blood stages. See, e.g., U.S. Pat. No. 5,853,739; International Publication No. WO 2006/124712. Orthologs of P25 are present in other *Plasmodium* species (such as *P. ovale, P. malariae*, and *P. knowlesi*) and are known to those of skill in the art.

Pfs25 sequences are publicly available. For example, GenBank accession number NC_004314.1 (incorporated herein by reference on Nov. 7, 2008) discloses a Pfs25 gene from *P. falciparum* 3D7. GenBank accession numbers XM_001347551.1 and XP_001347587.1 (incorporated herein by reference on Nov. 7, 2008) disclose *P. falciparum* 3D7 Pfs25 cDNA and protein sequences respectively. In a particular example, a Pfs25 protein is the amino acid sequence of SEQ ID NO: 7.

Pvs25 sequences are also publicly available. For example, GenBank accession number NC_009911.1 (incorporated herein by reference on Nov. 7, 2008) discloses a Pvs25 gene from *P. vivax* Sal-1. GenBank accession numbers XM_001608410.1 and XP_001608460.1 (incorporated herein by reference on Nov. 7, 2008) disclose *P. vivax* Sal-1

Pvs25 cDNA and protein sequences respectively. In a particular example, a Pvs25 protein is the amino acid sequence of SEQ ID NO: 8.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic compounds or molecules, such as one or more peptide conjugate, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a carrier. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Purified: The term "purified" does not require absolute purity; rather, it is intended as a relative term. Thus, for example, a purified peptide, protein, parasite, or other active compound is one that is isolated in whole or in part from naturally associated proteins and other contaminants. In certain embodiments, the term "substantially purified" refers to a peptide, protein, parasite or other active compound that has been isolated from a cell, cell culture medium, or other crude preparation and subjected to fractionation to remove various components of the initial preparation, such as proteins, cellular debris, and other components.

Recombinant: A recombinant nucleic acid, protein or parasite is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.*, 2:482, 1981); Needleman and Wunsch (*J. Mol. Biol.*, 48:443, 1970); Pearson and Lipman (*Proc. Natl. Acad. Sci.*, 85:2444, 1988); Higgins and Sharp (*Gene*, 73:237-44, 1988); Higgins and Sharp (*CABIOS*, 5:151-53, 1989); Corpet et al. (*Nuc. Acids Res.*, 16:10881-90, 1988); Huang et al. (*Comp. Appls. Biosci.*, 8:155-65, 1992); and Pearson et al. (*Meth. Mol. Biol.*, 24:307-31, 1994). Altschul et al. (*Nature Genet.*, 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, *Proc. Natl. Acad. Sci.* 85:2444-2448, 1988) may be used to perform sequence comparisons (Internet Program © 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.*, 215:403-10, 1990; Gish and States, *Nature Genet.*, 3:266-72, 1993; Madden et al., *Meth. Enzymol.*, 266:131-41, 1996; Altschul et al., *Nucleic Acids Res.*, 25:3389-402, 1997; and Zhang and Madden, *Genome Res.*, 7:649-56, 1997.

Orthologs (equivalent to proteins of other species) of proteins are in some instances characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, at least 98%, or at least 99% sequence identity. In addition, sequence identity can be compared over the full length of one or both binding domains of the disclosed fusion proteins.

When significantly less than the entire sequence is being compared for sequence identity, homologous sequences will typically possess at least 80% sequence identity over short windows of 10-20, and may possess sequence identities of at least 85%, at least 90%, at least 95%, 96%, 97%, 98%, or at least 99% depending on their similarity to the reference sequence. Sequence identity over such short windows can be determined using LFASTA; methods are described at the NCSA website. One of skill in the art will appreciate that these sequence identity ranges are provided for guidance only; it is entirely possible that strongly significant homologs could be obtained that fall outside of the ranges provided. Similar homology concepts apply for nucleic acids as are described for protein. An alternative indication that two nucleic acid molecules are closely related is that the two molecules hybridize to each other under stringent conditions.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Subject: Living multi-cellular vertebrate organisms, a category that includes both human and non-human mammals. Subjects include veterinary subjects, including livestock such as cows and sheep, rodents (such as mice and rats), and non-human primates.

Therapeutically effective amount: A quantity of a specified agent sufficient to achieve a desired effect in a subject being treated with that agent. For example, this may be the amount of a malaria protein or peptide conjugate useful for eliciting an immune response in a subject and/or for preventing infection by malaria. Ideally, in the context of the present disclosure, a therapeutically effective amount of a malaria protein or peptide conjugate is an amount sufficient to increase resistance to, prevent, ameliorate, and/or treat infection caused by malaria parasite in a subject without causing a substantial cytotoxic effect in the subject. The effective amount of a malaria protein or peptide conjugate useful for increasing resistance to, preventing, ameliorating, and/or treating infection in a subject will be dependent on, for example, the subject being treated, the manner of administration of the therapeutic composition and other factors.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. Sequences associated with GenBank Accession Numbers as of Nov. 7, 2008 are herein incorporated by reference. In case of conflict, the present specification, including explanations of terms, will control. In addition, the materials, methods, and examples are illustrative only and not intended to be limiting.

III. Overview of Several Embodiments

Disclosed herein are immunogenic conjugates which elicit an immune response to *Plasmodium* proteins. In some examples, the immunogenic conjugates provided herein can elicit an immune response to both sexual and asexual stages of *Plasmodium* (such as *P. falciparum, P. vivax, P. ovale, P. malariae*, or *P. knowlesi*). The disclosed immunogenic conjugates include conjugates of a *Plasmodium* sexual stage surface protein (such as P25, P28, P48/45, or P230 from *P. falciparum, P. vivax, P. ovale, P. malariae*, or *P. knowlesi*) and a *Plasmodium* circumsporozoite protein (CSP; such as CSP from *P. falciparum, P. vivax, P. ovale, P. malariae*, or *P. knowlesi*), or immunogenic portions thereof. In additional examples, the immunogenic conjugates provided herein can elicit an immune response to *Plasmodium* CSP. In some examples, the disclosed immunogenic conjugates include a full length CSP, a modified CSP, or an immunogenic portion of CSP (such as at least one NANP (SEQ ID NO: 1) repeat or variant thereof, or a T-cell epitope of a CSP) conjugated to CSP or an immunogenic portion thereof and/or an immunogenic carrier protein.

In some examples, the disclosed immunogenic conjugates include one or more *Plasmodium* sexual stage surface protein or an immunogenic portion thereof. The sexual stage surface proteins are a family of proteins expressed in *Plasmodium* sexual stage on the surface of gametocytes or ookinetes. Members of the sexual stage surface protein family include P25, P28, P48/45, and P230. Antibodies that target sexual stage surface proteins can potentially reduce or block fertilization and/or reduce or prevent transmission of the *Plasmodium* microorganism.

In some examples, the sexual stage surface protein is P25, a cysteine-rich mosquito stage antigen of about 25 kDa (see, e.g., Kaslow et al., *Nature* 333:74-76, 1988; Malkin et al., *Vaccine* 23:3131-3138, 2005). The P25 protein is composed of four tandem epidermal growth factor-like domains and is expressed on zygotes and mature ookinete stages of parasites within mosquitoes. Because P25 is only expressed in the mosquito midgut and not in the vertebrate host, these proteins have not been under selection pressure by the host immune system and antigenic variation of P25 appears to be more limited than most vaccine candidates present in pre-erythrocytic and asexual blood stages. See, e.g., U.S. Pat. No. 5,853,739; International Publication No. WO 2006/124712. In particular examples, the P25 protein utilized in the disclosed compositions is *P. falciparum* Pfs25 protein (such as GenBank accession number XP_001347587.1 or SEQ ID NO: 7), *P. vivax* Pvs25 protein (such as XP_001608460.1 or SEQ ID NO: 8), P25 protein orthologs from other *Plasmodium* species (such as *P. ovale, P. malariae,* or *P. knowlesi*), or variants thereof that retain immunogenicity.

In further examples, the sexual stage surface protein is P28, an approximately 28 kDa protein expressed on the zygote and ookinete surfaces during the mosquito stage of *Plasmodium* infection. P28 is structurally similar to P25, with four tandem epidermal growth factor-like domains (see, e.g., Duffy and Kaslow, *Inf. Immun.* 65:1109-1113, 1997). In particular examples, the P28 protein utilized in the disclosed conjugates is *P. falciparum* Pfs28 protein (such as GenBank accession number L25843), *P. vivax* Pvs28 protein (such as GenBank accession numbers AF083503, XM_001608411, EU514789, or AB091745), P28 protein orthologs from other *Plasmodium* species (such as *P. ovale, P. malariae,* or *P. knowlesi*), or variants thereof that retain immunogenicity.

In additional examples, the sexual stage surface protein is P48/45, a protein expressed by male and female *Plasmodium* gametes containing two six cysteine domains (van Dijk et al., *Cell* 104:153-164, 2001). Antibodies against Pfs48/45 have been shown to block or reduce transmission of the *P. falciparum* parasite (see, e.g., Outchkourov et al., *Proc. Natl. Acad. Sci. USA* 105:4301-4305, 2008). In particular examples, the P48/45 protein utilized in the disclosed conjugates is *P. falciparum* Pfs48/45 protein (such as GenBank accession number Z22145), *P. vivax* Pvs48/45 protein (such as GenBank accession number XP_001614246.1), P45/48 protein orthologs from other *Plasmodium* species (such as *P. ovale, P. malariae,* or *P. knowlesi*), or variants thereof that retain immunogenicity.

In further examples, the sexual stage surface protein is P230, a gametocyte surface antigen that is retained on the surface of gametes following emergence (see, e.g., U.S. Pat. No. 5,733,772). Antibodies against Pfs230 have been shown to block or reduce transmission of the malaria parasite. (see, e.g., Healer et al., *Infect. Immun.* 65:3017-3023, 1997). In particular examples, the P230 protein utilized in the disclosed conjugates is *P. falciparum* Pfs230 protein (such as GenBank accession number L08135 or AF269242), *P. vivax* Pvs230 protein (such as GenBank accession number XM_001613322.1 or XM_001612970), P230 protein orthologs from other *Plasmodium* species (such as *P. ovale, P. malariae,* or *P. knowlesi*), or variants thereof that retain immunogenicity.

In some examples, the disclosed immunogenic conjugates include *Plasmodium* CSP or an immunogenic portion thereof. CSP is a major parasite surface protein during the sporogonic cycle that covers the surface of *Plasmodium* sporozoites, which are transmitted from the mosquito salivary gland to host hepatocytes. It is highly immunogenic, and in endemic areas high antibody titers against this protein are observed in circulating blood. See, e.g., Dame et al., *Science* 225:593-599, 1985; Zavala et al., *Science* 228:1436-1440, 1985; International Publication No. WO 2008/107370.

In particular examples, the CSP utilized in the disclosed conjugates is *P. falciparum* CSP (such as GenBank accession number XP_001351122.1 or SEQ ID NO: 6), *P. vivax* CSP (such as GenBank accession number XP_001616893.1), CSP orthologs from other *Plasmodium* species (such as *P. ovale, P. malariae,* or *P. knowlesi*), or variants thereof that retain immunogenicity.

Immunogenic portions of CSP are known to one of skill in the art. In some examples, the *Plasmodium* CSP includes at least one multiply repeated amino acid motif, which forms an immunodominant epitope of CSP. In one example, this motif is NANP (SEQ ID NO: 1) in *P. falciparum* CSP (see, e.g., Dame et al., *Science* 225:593-599, 1985; Zavala et al., *Science* 228:1436-1440, 1985; International Publication No. WO 2008/124712). In other examples, the immunogenic portion of CSP includes variants of the multiply repeated *P. falciparum* NANP (SEQ ID NO: 1) motif, such as NPNA (SEQ ID NO: 2), PNAN (SEQ ID NO: 3), or ANPN (SEQ ID NO: 4). One of skill in the art can recognize immunodominant repeat motifs from *Plasmodium* CSP. In additional, non-limiting examples, the CSP repeated motif includes (D/A)GQPAGDRA (SEQ ID NO: 9) from *P. vivax* VK210 CSP, (G/D)NGPGANGA (SEQ ID NO: 10) from *P. vivax* VK247 CSP, NAAG (SEQ ID NO: 11) from *P. malariae* CSP, QAQGDGANGQP (SEQ ID NO: 12) from *P. knowlesi* CSP, or APGANQEGGAA (SEQ ID NO: 13) from *P. ovale* CSP.

In some examples, the end group of the CSP repeat motif can affect the immunogenicity of the conjugate containing the repeat. The ending amino acid group of the repeat can be Asn, Ala, or Pro. In particular examples, the end group is Asn. In other examples, the end group is Pro.

*Plasmodium* CSP also includes immunogenic portions which are T cell epitopes, such as a CSP universal T cell epitope. In a particular example, the CSP universal T-cell epitope is from *P. falciparum* and has the sequence EYLNKIQNSLSTEWSPCSVT (SEQ ID NO: 14) (see, e.g. U.S. Pat. Publ. 2005/0249750), variants thereof that retain immunogenicity, or equivalent sequences from orthologous CSP proteins. In another example, the CSP T cell epitope is from *P. falciparum* and has the sequence $(DPNANPNV)_2$ (SEQ ID NO: 15) (see, e.g. U.S. Pat. Publ. 2005/0249750), variants thereof that retain immunogenicity, or equivalent sequences from orthologous CSP proteins.

Provided herein are immunogenic conjugates that include at least one *Plasmodium* sexual stage surface protein (for example, P25, P28, P48/45, or P230) covalently linked to at least one *Plasmodium* CSP, or an immunogenic portion thereof, wherein the conjugate elicits an immune response to the sexual stage surface protein and the CSP in a subject. In some embodiments the immunogenic conjugate includes at least one sexual stage surface protein (such as one, two, three, four, five, or more sexual stage surface proteins) covalently linked to at least one CSP (such as one, two, three, four, or five CSPs). In a particular, non-limiting example, the immunogenic conjugate includes two P25 proteins (such as Pfs25 or Pvs25) covalently linked to one CSP (such as Pfs25-AH-Pfs25 linked to CSP). In another example, the immunogenic conjugate includes one P25 protein (such as Pfs25 or Pvs25) covalently linked to one CSP (such as Pfs25-CSP).

The immunogenic conjugates disclosed herein also include conjugates having at least one *Plasmodium* sexual stage surface protein (such as P25, P28, P48/45, or P230) covalently linked to at least one CSP NANP repeat or a variant thereof (such as at least one NANP (SEQ ID NO: 1) repeat, at least one NPNA (SEQ ID NO: 2) repeat, at least one PNAN (SEQ ID NO: 3) repeat, at least one ANPN (SEQ ID NO: 4) repeat, or a combination of two or more thereof). In some examples, the conjugate includes two to ten NANP repeats or variants thereof (such as two, three, four, five, six, seven, eight, nine, or ten repeats). In particular examples, the conjugate includes three to six NANP repeats or variants thereof.

In some examples, the conjugate includes two sexual stage surface proteins (such as two Pfs25 proteins) covalently linked to (NANP)$_x$, (NPNA)$_x$, (PNAN)$_x$, or (ANPN)$_x$, where x is one or more (for example, 1-10, such as 2-8 or 3-6, for example, 4 or 5). In particular non-limiting examples, the conjugate includes two P25 proteins (such as Pfs25 or Pvs25) covalently linked to (NANP)$_4$ (SEQ ID NO: 16) or (NANP)$_5$ (SEQ ID NO: 17), two P25 proteins (such as Pfs25 or Pvs25) covalently linked to (NPNA)$_4$ (SEQ ID NO: 18) or (NPNA)$_5$ (SEQ ID NO: 19), two P25 proteins (such as Pfs25 or Pvs25) covalently linked to (PNAN)$_4$ (SEQ ID NO: 20) or (PNAN)$_5$ (SEQ ID NO: 21), or two P25 proteins (such as Pfs25 or Pvs25) covalently linked to (ANPN)$_4$ (SEQ ID NO: 22) or (ANPN)$_5$ (SEQ ID NO: 23).

Also provided herein are immunogenic conjugates including at least one NANP (SEQ ID NO: 1) repeat or variant thereof from *P. falciparum* CSP covalently linked to at least one other immunogenic protein, wherein the conjugate elicits an immune response to the repeat in a subject. In some examples, the conjugate includes two to ten NANP repeats or variants thereof (such as two, three, four, five, six, seven, eight, nine, or ten repeats). In some examples, the repeat from CSP is selected from the group consisting of NPNA (SEQ ID NO: 2), PNAN (SEQ ID NO: 3), and ANPN (SEQ ID NO: 4). In particular examples the immunogenic conjugate includes (NANP)$_x$, (NPNA)$_x$, (PNAN)$_x$, or (ANPN)$_x$, where x is one or more (for example, 1-10, such as 2-8 or 3-6, for example, 4 or 5), for example, (NANP)$_4$ (SEQ ID NO: 16) or (NANP)$_5$ (SEQ ID NO: 17), (NPNA)$_4$ (SEQ ID NO: 18) or (NPNA)$_5$ (SEQ ID NO: 19), (PNAN)$_4$ (SEQ ID NO: 20) or (PNAN)$_5$ (SEQ ID NO: 21), or (ANPN)$_4$ (SEQ ID NO: 22) or (ANPN)$_5$ (SEQ ID NO: 23) covalently linked to at least one other immunogenic protein.

The other immunogenic protein (sometimes referred to as a "carrier" protein) ideally has the properties of being immunogenic by itself, usable in a subject, and of a size that can be easily purified and conjugated to at least one other protein or peptide. The carrier protein can be an immunogenic protein from *Plasmodium*, such as CSP or Pfs25, or an immunogenic protein other than a *Plasmodium* protein, such as a human pathogen protein or other protein that elicits an immune response. Suitable carrier proteins are known to one of skill in the art. In particular examples, the other immunogenic protein (carrier protein) is bovine serum albumin (BSA), ovalbumin, tetanus toxoid, diphtheria toxoid, cholera toxin, *Clostridium difficile* toxin A, *C. difficile* toxin B, or *Pseudomonas aeruginosa* recombinant exoprotein A. In particular examples, the one or more NANP (SEQ ID NO:1) repeat or variant thereof is covalently linked to BSA. In another specific example, the immunogenic conjugate is (NPNA)$_5$ (SEQ ID NO: 19) covalently linked to CSP. In another specific example, the immunogenic conjugate is (PNAN)$_5$ (SEQ ID NO: 21) covalently linked to diphtheria toxoid. In a further specific example, the immunogenic conjugate is (NANP)$_4$ (SEQ ID NO: 16) covalently linked to tetanus toxoid.

Also provided are immunogenic conjugates that include a peptide comprising at least one *Plasmodium* T-cell epitope and at least four NANP repeats covalently linked to at least one other immunogenic protein. In some examples, the *Plasmodium* T-cell epitope is from CSP, such as the *P. falciparum* CSP peptide EYLNKIQNSLSTEWSPCSVT (SEQ ID NO: 14) or (DPNANPNV)$_2$ (SEQ ID NO: 15). In particular examples, the conjugate also includes four, five, or six NANP repeats, such as (NANP)$_4$ (SEQ ID NO: 16), (NANP)$_5$ (SEQ ID NO: 17), or (NANP)$_6$ (SEQ ID NO: 24) linked to the *Plasmodium* T cell epitope.

Also provided are immunogenic conjugates that include a *Plasmodium* T-cell epitope and at least one NANP (SEQ ID NO: 1) repeat, at least one PNAN (SEQ ID NO: 2) repeat, at least one NPNA (SEQ ID NO: 3) repeat, or at least one ANPN (SEQ ID NO: 4) repeat covalently linked to at least one other immunogenic protein. In some examples, the *Plasmodium* T-cell epitope is from CSP, such as the *P. falciparum* CSP peptides EYLNKIQNSLSTEWSPCSVT (SEQ ID NO: 14) or (DPNANPNV)$_2$ (SEQ ID NO: 15). In some examples, the conjugate includes three, four, five, or six repeats or combinations thereof. In particular examples, the conjugate includes at least one *P. falciparum* T-cell epitope and (NANP)$_4$ (SEQ ID NO: 16) or (NANP)$_5$ (SEQ ID NO: 17), (NPNA)$_4$ (SEQ ID NO: 18) or (NPNA)$_5$ (SEQ ID NO: 19), (PNAN)$_4$ (SEQ ID NO: 20) or (PNAN)$_5$ (SEQ ID NO: 21), or (ANPN)$_4$ (SEQ ID NO: 22) or (ANPN)$_5$ (SEQ ID NO: 23) covalently linked to at least one other immunogenic protein. The other immunogenic protein can be an immunogenic protein from *Plasmodium*, such as CSP or Pfs25, or an immunogenic protein other than a *Plasmodium* protein, such as a human pathogen protein or other protein that elicits an immune response. In particular examples, the other immunogenic protein is bovine serum albumin (BSA), ovalbumin, tetanus toxoid, diphtheria toxoid, cholera toxin, *Clostridium difficile* toxin A, *C. difficile* toxin B, or *Pseudomonas aeruginosa* recombinant exoprotein A. In one specific example, the conjugate includes (NANP)$_4$-EYLNKIQNSLSTEWSPCSVT (SEQ ID NO: 25) covalently linked to BSA.

One of skill in the art will recognize that variants of the proteins and peptides utilized in the disclosed immunogenic conjugates may also be useful for generating an immune response. Such variants include one or more naturally occurring or recombinantly introduced nucleotide or amino acid substitutions, such as a protein or peptide having at least about 80% sequence identity (for example at least about 85%, about 90%, about 95%, about 96%, about 97%, about 98%, or even about 99% sequence identity) to the protein or peptide. Methods of introducing nucleotide or amino acid substitutions are well known to those of skill in the art. For instance, protocols are provided in Sambrook et al. (ed.), *Molecular Cloning: A Laboratory Manual*, 2$^{nd}$ ed., vol. 1-3, Cold Spring Harbor Laboratory Press, Cold Spring Harbor, N.Y., 1989.

The simplest modifications involve the substitution of one or more amino acids for amino acids having similar physiochemical and/or structural properties. These so-called conservative substitutions are likely to have minimal impact on the activity and/or structure of the resultant protein (such as immunogenicity). Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

Variants of the disclosed proteins or peptides may also include modified proteins or peptides (such as deletion of a sequence that decreases or interferes with immunogenicity or addition of a sequence that facilitates cloning or purification of a protein). In particular examples, the sexual stage surface protein and/or CSP contains an additional sequence to facilitate purification of recombinantly expressed protein (such as a 6xHis tag). In additional examples, the GPI-anchoring motif of the CSP may be removed to enhance immunogenicity (see, e.g., Bruna-Romero et al., *Vaccine* 22:3575-3584, 2004) and/or eight amino acids at the amino-terminus of the CSP may be removed. A particular, non-limiting example of a modified CSP has the nucleic acid and amino acid sequence of SEQ ID NOs: 5 and 6, respectively, which lacks the GPI anchor and includes six terminal histidine residues. In other embodiments, the CSP protein includes the amino acid sequence of SEQ ID NO: 6 without the six terminal histidine residues.

The highest antibody levels for conjugates of sexual stage surface protein (such as P25, P28, P48/45, or P230) and CSP are generally obtained for conjugates having a molar ratio of sexual stage surface protein (for example, Pfs25 or Pvs25) to the other protein or peptide (such as CSP or immunogenic portions thereof, for example NANP (SEQ ID NO: 1) repeats or variants thereof) of greater than 1:1, such as about 1.1:1 to about 5:1 (for example, about 1.2:1 to about 4:1, about 1.3:1 to about 3:1, or about 1.4:1 to about 2.5:1). In some examples, the ratio of sexual stage surface protein to the other protein or peptide of the conjugate is about 2:1. In a particular example, the ratio of Pfs25 to CSP repeat sequence is about 2:1. The methods of preparing conjugates described herein yield reaction products with a distribution of molecular weights. The resulting reaction mixture can be fractionated into fractions having different molecular weights. In specific examples, the conjugate has a molecular mass of about 50-250 kDa by SDS-PAGE.

In some examples, the described immunogenic conjugates include NANP (SEQ ID NO: 1), NPNA (SEQ ID NO: 2), PNAN (SEQ ID NO: 3), or ANPN (SEQ ID NO: 4) repeat chains covalently linked to another immunogenic protein (for example P25, CSP, BSA, or another carrier protein). The number of repeat chains linked to the second protein can vary, for example as a result of the starting amount of the repeat chains and other protein in the linking reaction or the number of functional groups on the protein. The number of chains (for example, the number of NANP (or variants thereof) repeat chains per BSA or the number of NANP (or variants thereof) repeat chains per P25) is generally from about five to about thirty, such as about ten to twenty. The optimal number of chains varies for each protein and can be determined by one of skill in the art.

IV. Linking Groups and Conjugation Reactions

The proteins or peptides described herein can be covalently linked to one another by suitable linkages. The covalent linkage may be a non-peptide linker (such as an amide linkage, a hydrazone linkage, or a thioether linkage) or a peptide linker.

In some examples, the conjugates described herein include proteins or peptides linked by non-peptide covalent linkages. Particular examples of non-peptide linkages useful for the conjugates described herein are described in U.S. Pat. Publication No. 2005/0271675; International Publication No. WO 2008/048945; Schneerson et al., *J. Exp. Med.* 152:361-376, 1980; Schneerson et al., *Proc. Natl. Acad. Sci. USA* 100: 8945-8950, 2003; Kubler-Kielb et al., *Proc. Natl. Acad. Sci. USA* 104:293-298, 2007. In some examples, the covalent linkage is an amide linkage, a hydrazone linkage, or a thioether linkage, particularly an amide linkage or a thioether linkage. Particular linking groups include adipic acid dihydrazide (ADH), N-succinimidyl-4-formylbenzoate (SFB), N-succinimidyl-3-bromoacetamidopropionate (SBAP), and N-succinimidyl-3-(2-pyridyldithio)-propionate (SPDP).

ADH or a suitable analog, such as a member of the group of compounds of the formula:

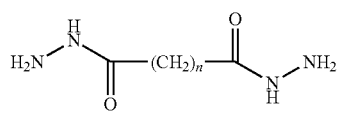

where n is one, two, three, four, or five, can be employed as a linking agent to yield an amide linkage. A carboxylic acid moiety of a protein or polypeptide (such as P25, CSP or a portion thereof, or another immunogenic protein) reacts with a hydrazide group of the linking agent to yield an amide linkage. In some examples, the reaction can be performed in two steps, the first step involving derivatization of the protein or polypeptide with the dihydrazide followed by a second step involving further reaction of the derivatized protein with another protein or polypeptide.

ADH or a suitable analog (as described above) and SFB (or a suitable analog) having the formula:

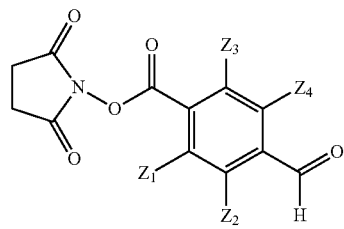

where Z is independently hydrogen, halogen (for example, fluorine, chlorine, bromine, or iodine), or lower alkyl (for example, $C_1$-$C_6$ alkyl), can be employed as a linking agent to yield a hydrazone linkage. The reaction is preferably performed in two steps. In the first step, an amine moiety of a protein or polypeptide (such as P25, CSP or a portion thereof, or another immunogenic protein) reacts with SFB to yield derivatized protein or polypeptide and separately a carboxylic acid moiety of another protein or polypeptide reacts with ADH to yield derivatized protein. In the second step, the two derivatives are reacted to yield a conjugate including a hydrazone linking group.

SBAP (or a suitable analog) having the formula:

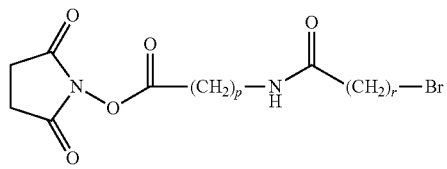

where p is one, two, three, four, five, six, seven, or eight and r is one, two, three, four, five, six, seven, or eight, and SPDP (or a suitable analog) having the formula:

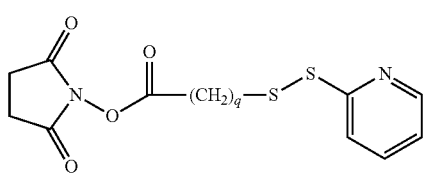

where q is one, two, three, four, five, six, seven, or eight, can be employed as linking agents to yield a thioether linkage.

The reaction is preferably performed in two steps. The first step involves reacting an amine moiety of a protein or polypeptide (such as P25, CSP or a portion thereof, or another immunogenic protein) with SBAP to yield a derivatized protein or polypeptide and separately reacting an amine moiety of another protein or polypeptide with SPDP to yield a derivatized protein. In the second step, the two derivatives are reacted to yield a conjugate including a thioether linking group.

In some conjugates a single type of linkage can be employed, or a mixture of two or more types of linkage can be employed. In particular examples the immunogenic conjugate includes two Pfs25 proteins covalently linked by an amide linking group which is in turn linked to a NANP repeat (or variant thereof) by a thioether linkage.

In particular examples, the conjugation reaction (such as a reaction linking at least two *Plasmodium* sexual stage surface proteins, or a reaction linking one or more *Plasmodium* sexual stage surface proteins to CSP or a portion thereof) is carried out in two steps. In other examples, the conjugation reaction is carried out in a single step. For a particular conjugate, one of skill in the art can determine whether a two-step or one-step conjugation reaction is advantageous, for example producing higher yields of conjugate.

In some examples, the conjugates described herein are linked by a peptide linkage. Linkers useful in the invention may, for example, be simply peptide bonds, or may comprise amino acids, including amino acids capable of forming disulfide bonds. In particular examples, the length of the linker is one to ten peptide bonds (such as 1, 2, 3, 4, 5, 6, 7, 8, 9, or 10 peptide bonds), one to twelve amino acids (such as 1, 2, 3, 4, 5, 6, 7, 8, 9, 10, 11, or, 12 amino acids), or a combination thereof. In some examples, the linker is one, two, three, four, or five amino acids (for example, arginine or lysine). It is desirable to use a linker that does not produce an immune reaction (or produces only a minimal immune reaction) in a host. One of skill in the art can determine whether a particular linker produces an immune reaction in a host.

V. Methods of Eliciting an Immune Response

Provided are methods of eliciting an immune response in a host by administering one or more immunogenic conjugates described herein to the host. In a particular example, the host is a human. The immunogenic conjugates disclosed herein can be used to produce an immune response that prevents infection with *Plasmodium* parasites, and can also be used to treat or inhibit infection with *Plasmodium* parasites.

In some examples, the method further includes selecting a host in need of enhanced immunity to *Plasmodium* (such as *P. falciparum, P. vivax, P. ovale, P. malariae*, and *P. knowlesi*). Hosts in need of enhanced immunity to *Plasmodium* include subjects who are at risk of malaria infection, subjects who have been exposed to *Plasmodium* parasites, and subjects who are infected with *Plasmodium* parasites. Residents of, or travelers to, countries or regions where malaria is endemic (such as Africa, Central and South America, the island of Hispaniola (Haiti and the Dominican Republic), Asia (including the Indian subcontinent, Southeast Asia and the Middle East), Eastern Europe, and the South Pacific) are at risk of contracting malaria, such as malaria caused by infection with *Plasmodium*. Additional factors that contribute to risk of infection with *Plasmodium* include the characteristics of the area, time of year, presence of malaria in the area, exposure to mosquito bites, and lack of preventive measures (such as anti-malarial drugs and/or insect repellant). The risk of malaria is generally higher in rural areas and low altitudes with warm temperatures. Risk of malaria is also increased in seasons with more rainfall and warmer temperatures, although transmission can occur at any time of the year. Exposure to mosquito bites, for example, being out of doors at night or sleeping without mosquito netting increases the risk of malaria infection.

The disclosed peptide conjugates, or immunogenic compositions thereof, can be administered to a subject by any of the routes normally used for introducing a composition into a subject. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

Immunogenic compositions are administered in any suitable manner, such as with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose administered to a subject in the context of the present disclosure should be sufficient to induce a beneficial therapeutic response in a subject over time, or to inhibit or prevent malaria infection. The dose required will vary from subject to subject depending on the species, age, weight and general condition of the subject, the severity of the infection being treated, the particular immunogenic composition being used and its mode of administration. An appropriate dose can be determined by one of ordinary skill in the art using only routine experimentation. Repeated immunizations may be necessary to produce an immune response in a subject. Immunization protocols (such as amount of immunogen, number of doses and timing of administration) can be determined experimentally, for example by using animal models (such as non-human primates) followed by clinical testing in humans.

Provided herein are pharmaceutical compositions (also referred to as immunogenic compositions) which include a therapeutically effective amount of the disclosed immunogenic conjugates alone or in combination with a pharmaceutically acceptable carrier. Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

The pharmaceutical compositions disclosed herein can additionally employ adjuvants conventionally found in pharmaceutical compositions in their art-established fashion and at their art-established levels. Thus, for example, the compositions can contain materials useful in physically formulating various dosage forms of the preferred embodiments. Adjuvants are commonly combined with immunogenic compositions (vaccines) for the purpose of improving immune response. Suitable adjuvants include aluminum hydroxide, aluminum phosphate, aluminum oxide, monophosphenyl lipid A, muramyl dipeptide, glucans, Quil A, Freund's incomplete adjuvant, or Freund's complete adjuvant. If aluminum hydroxide (alum) or aluminum phosphate is used, the amount used preferably is no more than 0.84 mg aluminum per dose.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinylseryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

VI. Methods of Assessing Immunogenic Response

The compositions and methods disclosed herein are useful for generating an immunogenic response in a host or subject. Methods of assessing an immune response to a composition are well known to one of skill in the art.

In some examples, an immune response to a composition, such as the disclosed immunogenic conjugates, is determined by assessing the production of antibodies to the composition. The method of detecting antibodies to the disclosed compositions in a sample can be performed, for example, by contacting a fluid or tissue sample from a subject immunized with the composition with a polypeptide of the composition and detecting the binding of the polypeptide to the antibody. A fluid sample of this method can comprise any biological fluid which could contain the antibody, such as cerebrospinal fluid, blood, bile plasma, serum, saliva and urine. Other possible examples of body fluids include sputum, mucus and the like.

Enzyme immunoassays such as IFA, ELISA and immunoblotting can be readily adapted to accomplish the detection of antibodies according to the methods of this disclosure. An ELISA method effective for the detection of the antibodies can, for example, be as follows: 1) bind the polypeptide to a substrate; 2) contact the bound polypeptide with a fluid or tissue sample containing the antibody; 3) contact the above with a secondary antibody bound to a detectable moiety which is reactive with the bound antibody (for example, horseradish peroxidase enzyme or alkaline phosphatase enzyme); 4) contact the above with the substrate for the enzyme; 5) contact the above with a color reagent; and 6) observe/measure color change or development.

Another immunologic technique that can be useful in the detection of antibodies uses monoclonal antibodies (mAbs) for detection of antibodies specifically reactive with the disclosed compositions in a competitive inhibition assay. Briefly, a sample is contacted with a polypeptide of this disclosure which is bound to a substrate (for example, a 96-well plate). Excess sample is thoroughly washed away. A labeled (for example, enzyme-linked, fluorescent, radioactive, etc.) mAb is then contacted with any previously formed polypeptide-antibody complexes and the amount of mAb binding is measured. The amount of inhibition of mAb binding is measured relative to a control (no antibody), allowing for detection and measurement of antibody in the sample.

As a further example, a micro-agglutination test can be used to detect the presence of antibodies to the disclosed compositions in a sample. Briefly, latex beads, red blood cells or other agglutinable particles are coated with a polypeptide of this disclosure and mixed with a sample, such that antibodies in the sample that are specifically reactive with the antigen crosslink with the antigen, causing agglutination. The agglutinated polypeptide-antibody complexes form a precipitate, visible with the naked eye or measurable by spectrophotometer.

In yet another example, a microsphere-based immunoassay can be used to detect the presence of antibodies in a sample. Briefly, microsphere beads are coated with a component of a composition of this disclosure (such as Pfs25, Pvs25, CSP, or an immunogenic portion thereof) and mixed with a sample, such that antibodies in the sample that are specifically reactive with the antigen bind the antigen. The bead-bound polypeptide-antibody complexes are allowed to react with fluorescent-dye labeled anti-species antibody (such as FITC-labeled goat anti-human IgM), and are measured using a detector (such as a LUMINEX® instrument).

In some examples, an immune response to a composition, such as the disclosed immunogenic conjugates, is determined by assessing the production of malaria transmission-blocking antibodies (such as antibodies to a sexual stage surface protein, for example P25, P28, P48/45, or P230). Transmission-blocking assays are well known to those of skill in the art (see, e.g., Quakyi et al., *J. Immunol.* 139:4213-4217, 1987). Briefly, serum containing a potentially transmission-blocking antibody is mixed with a *Plasmodium* gametocyte culture and fed to *Anopheles* mosquitoes through a membrane feeding apparatus. Mosquitoes are kept for a sufficient period of time to allow the development of mature oocysts. Infectivity is assessed by staining the mosquito midguts to detect oocysts (for example, staining with mercurochrome) and counting the number of oocysts per midgut. Percent inhibition of transmission is calculated by the formula: 100×(oocyst # negative control−oocyst # test)/oocyst # negative control, where the test and negative control sera are matched for fold dilution in the assay.

In additional examples, an immune response to a composition, such as the disclosed immunogenic conjugates is determined by assessing the protective effect against infection produced by immunization with the disclosed compositions. Briefly, a host (such as a non-human primate, for example rhesus monkey or chimpanzee) is immunized with one or more of the disclosed immunogenic compositions. Following a sufficient period of time to allow development of an immune response, the host is challenged with viable *Plasmodium* parasites. The infection is monitored by examination of blood smears for the presence of parasites in the blood. A reduction in the number of parasites in immunized hosts as compared to control hosts indicates that an immune response developed to the composition.

In further examples, an immune response to a composition, such as the disclosed immunogenic conjugates is determined by assessing T-cell cytokine production. For example, a sample containing T-cells (such as blood, for example, peripheral blood mononuclear cells) can be obtained from a subject which has been administered one or more of the immunogenic conjugates described herein. The T-cells are stimulated with the immunogenic conjugate or a portion thereof (for example, a *Plasmodium* sexual stage surface antigen, CSP, or a CSP repeat) and cytokine production (such as gamma interferon, interleukin-2, interleukin-4, interleukin-5 interleukin-6, interleukin-10, interleukin-12, interleukin-13, granulocyte/macrophage colony-stimulating factor, or tumor necrosis factor-α) is measured. Methods of measuring cytokines are well known to one of skill in the art and include, but are not limited to, ELISA, ELISPOT, or flow cytometry (such as the FASTIMMUNE™ Cytokine System, Becton Dickinson).

The present disclosure is illustrated by the following non-limiting Examples.

EXAMPLE 1

Preparation of *Plasmodium falciparum* Protein Conjugates

Pfs25-Pfs25 conjugates were linked by amide linkages as described in Kubler-Kiehl et al., *Proc. Natl. Acad. Sci. USA* 104:293-298, 2007 (incorporated herein by reference).

Recombinant *Plasmodium falciparum* ookinete surface protein Pfs25 was derivatized with adipic acid dihydrazide (ADH) by formation of amide bonds between carbodiimide activated aspartic and glutamic acid carboxyl groups of the protein. In some examples, the Pfs25-AH-Pfs25 conjugate was prepared by a one-step procedure (FIG. 1A). Derivatized Pfs25 (15 mg/ml) was reacted with 0.006 M ADH (6% w/w) in the presence of 0.1 M 1-ethyl-3-[3-dimethylaminopropyl] carbodiimide hydrochloride (EDC) at pH 5.1 for 4 hours at room temperature and tumbled overnight at 4-8° C. The reaction mixture was dialyzed against phosphate buffered saline (PBS) and then passed through a 1×90 cm Sepharose CL-6B column (Amersham Pharmacia, Pittsburgh, Pa.) in 0.2 M NaCl. Fractions reacting with anti-Pfs25 by immunodiffusion were divided into two pools according to their molecular masses, based on column chromatography and SDS-PAGE profiles (fraction F1, higher molecular weight fraction; fraction F2, lower molecular weight fraction).

Figure 1B:
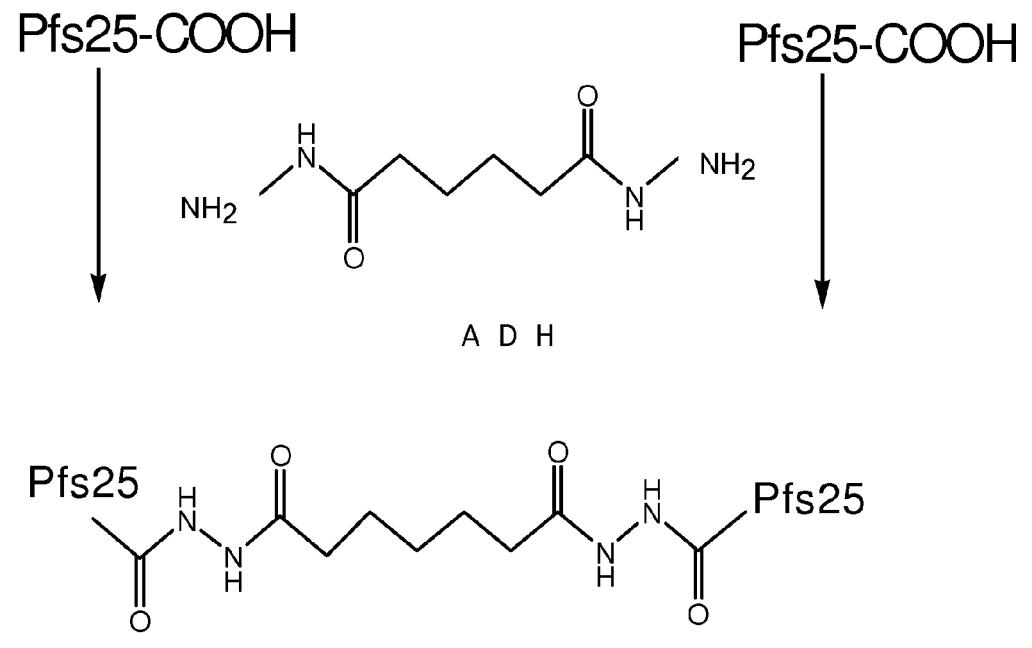

In other examples, the Pfs25-AH-Pfs25 conjugate was prepared by a two-step procedure (FIG. 1B). Pfs25 was derivatized with ADH as described in Schneerson et al., *J. Exp. Med.* 152:361-376, 1980. Equal amounts of Pfs25-AH and Pfs25 were mixed at 7.5 mg/ml each and reacted with 0.05 M EDC at pH 5.8 for 4 hours at room temperature and tumbled overnight at 4-8° C. The reaction mixture was then treated as above.

Figure 2:
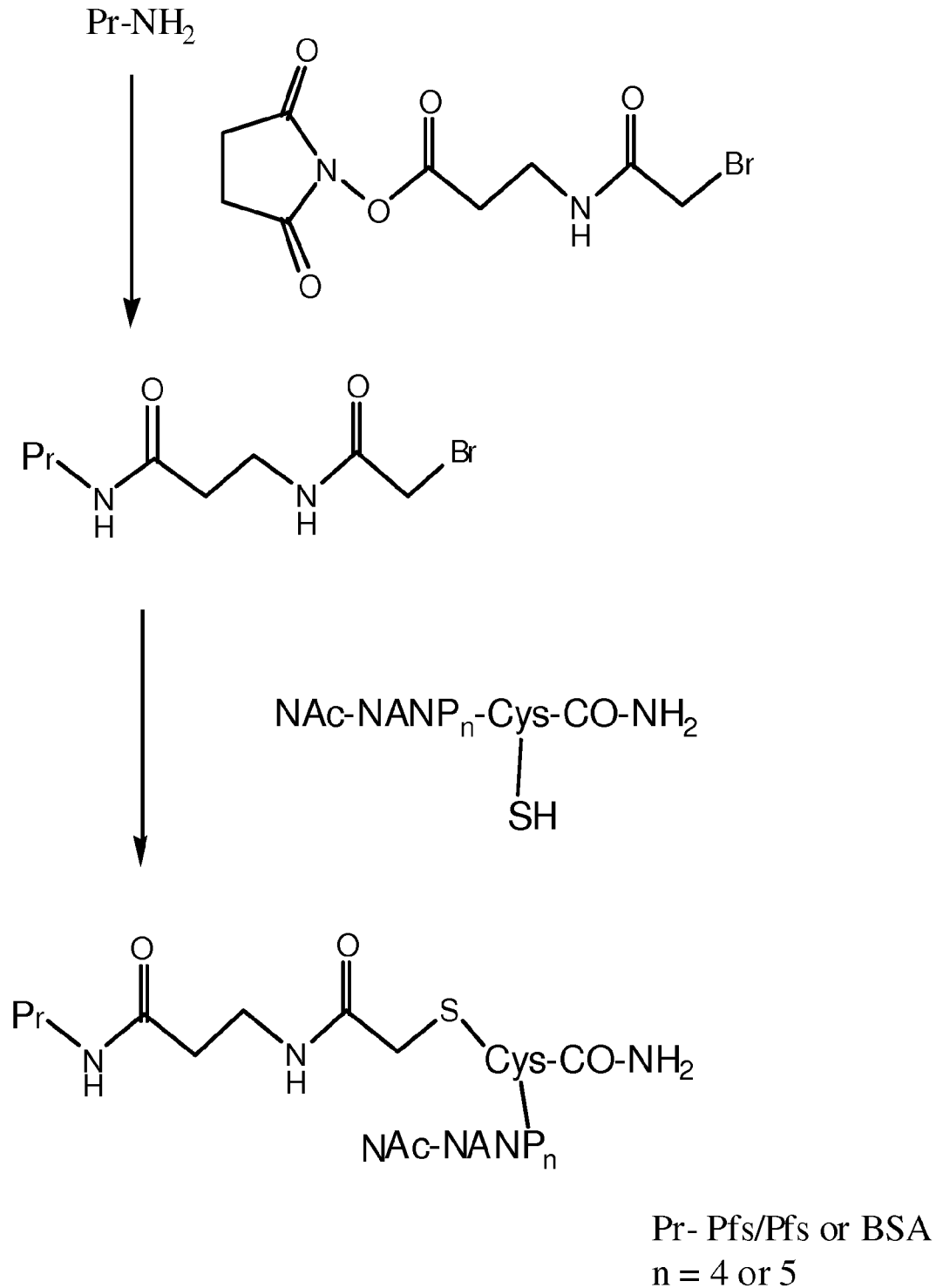
FIG. 2 is a diagram showing protein conjugation to NANP repeats by formation of a thioether linkage.

Conjugates of Pfs25-AH-Pfs25 to another protein or conjugates of other proteins were prepared by bromoacetylating the protein and conjugating a second protein with a terminal cysteine through formation of a thioether linkage as described in Schneerson et al., *Proc. Natl. Acad. Sci. USA* 100:8945-8950, 2003 and Kubler-Kielb et al., *Infect. Immun.* 74:4744-4749, 2006 (incorporated herein by reference). FIG. 2 shows a diagram of the method of conjugating a protein (such as Pfs25-Pfs25 or BSA) to NANP repeats. Protein (such as Pfs25-Pfs25 conjugate, BSA, or other protein) was bromoacetylated using succinimidyl 3-(bromoacetamido) propionate (SBAP; 11 mg in 50 μl of dimethyl sulfoxide), added in 10 μl aliquots. After 60 minutes, the reaction mixture was passed through a 1×90 cm Sepharose CL-6B column in 0.01 M phosphate/0.2 M NaCl/0.05% glycerol, pH 7.2. Fractions containing bromoacetoamidopropionyl-ε-Lys-NH-protein (Br-protein) were collected and assayed for protein, free —NH₂, antigenicity, and molecular mass. Protein or peptide to be conjugated to the bromoacetylated protein (such as CSP or NANP, NPNA, ANPN, or PNAN repeats) with a carboxy-terminal cysteine residue were adjusted to pH 7.6 with 1 M NaOH and Br-protein (25 mg) in 1.5 ml of PBS/3% glycerol/0.005 M EDTA, pH 7.6 was added. After 1 hour, the reaction mixture was transferred to a vial, capped, and tumbled overnight at room temperature. 2-Mercaptoethanol (1 μl) was added to quench the remaining bromoacetyl groups in Br-protein. After 30 minutes, the reaction mixture was passed through a 1×90 cm Sepharose CL-6B column in 0.01 M phosphate/0.2 M NaCl/0.05% glycerol, pH 7.2. Fractions containing protein conjugates were pooled and assayed for protein concentration, antigenicity, and molecular mass.

EXAMPLE 2

Immunogenicity of Pfs25-NANP Conjugates

Methods

Pfs25-Pfs25 conjugated to NANP peptides was prepared as described in Example 1. 5-6 week-old NIH general purpose mice (n=10) were injected subcutaneously with 2.5 μg of NANP as conjugate 2 weeks apart. Mice were exsanguinated 7 days after the second or third injection and IgG levels were measured.

Serum IgG antibodies were measured by ELISA. Ninety-six well plates were coated with 10 μg of antibody/ml PBS. Plates were blocked with 0.5% BSA for 1 hour at room temperature and incubated with test sera overnight, followed by phosphatase-labeled affinity-purified goat anti-mouse IgG (KPL, Gaithersburg, Md.) for 4 hours. A MRX reader (Dynatech, Chantilly, Va.) was used to record the optical density.

Transmission-blocking activity was determined as described in Kubler-Kielb et al., Proc. Natl. Acad. Sci USA 104:293-298, 2007. Sera from mice immunized with Pfs25/NANP conjugates formulated with AI-hydrogel were pooled and heat inactivated at 56° C. for 15 minutes. The sera were then diluted serially with a naïve human serum pool to minimize non-specific inhibitory effect of mouse sera. For each pool tested, a preimmune serum, diluted in parallel to the immune sera was used for baseline quantification of gametocyte. The diluted sera were mixed with a P. falciparum gametocyte culture (NF54 line) and fed to Anopheles stephensi (Nijmegen strain) through a membrane feeding apparatus. Mosquitoes were kept for 8 days to allow parasites to develop into mature oocysts. Infectivity was measured by dissecting at least 20 mosquitoes per serum sample, staining the midguts with mercurochrome (Sigma-Aldrich, St. Louis, Mo.), and counting the number of oocysts per midgut. To calculate the percent reduction of oocysts, the following formula was used: 100×(oocyst # negative control−oocyst # test)/oocyst # negative control, were test and negative control sera were matched in serial dilution fold.

Results

Some of the constructs with Pfs25-Pfs25/NANP conjugates induced long-lasting antibody responses to both their components (Table 1). Use of the adjuvant aluminum hydroxide (alum) improved the immune response to both Pfs25 and CSP. In addition, the levels of Pfs25 and CSP antibodies rose three months after the second injection in mice injected with the Pfs25-AH-Pfs25/NANP$_5$ conjugate with aluminum hydroxide as adjuvant. (NPNA)$_5$-Pfs25 monomer adsorbed on alum was a poor immunogen and was not an effective carrier for CSP peptide. This indicates that Pfs25 conjugates (such as Pfs25-AH-Pfs25) are more effective as a carrier for CSP peptides.

TABLE 1

Anti-Pfs25 and anti-CSP IgG levels in mice injected with Pfs-25/NANP conjugates

| Preparation | Ratio Pfs:NANP | NANP Chains per Pfs25 Protein | IgG by ELISA Anti-Pfs/Anti-Mal 2$^{nd}$ Inj. | 3$^{rd}$ Inj. |
|---|---|---|---|---|
| Pfs25-AH-Pfs25 | NA | NA | 10.5/— | 354/— |
| Pfs25-AH-Pfs25/(NANP)$_4$ #1 | 1.4:1.0 | 9 | 0.4/6.6 | 3.7/74.2 |
| Pfs25-AH-Pfs25/(NANP)$_5$ #2 | 0.9:1.0 | 11 | 0.001/1.1 | 1.4/9.0 |
| Pfs25-AH-Pfs25/(NANP)$_5$ #3 | 2.0:1.0 | 5 | 0.8/3.3 | 41/32 |
| Pfs25-AH-Pfs25/(NANP)$_5$ #3 on alum | 2.0:1.0 | 5 | 87/53 | 321/165 |
| Pfs25-AH-Pfs25/(NANP)$_5$ #3 on alum (3 months later) | 2.0:1.0 | 5 | 524/120 | |

Anti-Pfs25 levels are expressed in mg/ml; anti-CSP levels are expressed in EU/ml.
NA = Not applicable The conjugates were also tested for antibody titer of anti-CSP antibodies and for the ability of anti-Pfs25 antibodies to block transmission of P. falciparum. All Pfs25-AH-Pfs25/NANP conjugates produced anti-CSP and anti-Pfs25 antibodies and reduced the percentage of oocysts in the transmission-blocking assay (Table 2). Pfs25-AH-Pfs25/(NANP)5 adsorbed on alum provided the highest immune response to both CSP and Pfs25, and the greatest reduction in oocysts. In addition, the levels of Pfs25 and CSP antibodies rose three months after the second injection in mice injected with the Pfs25-AH-Pfs25/(NANP)$_5$ conjugate with aluminum hydroxide as adjuvant and provided complete transmission-blocking activity. This construct provided higher anti-Pfs25 antibodies and transmission blocking activity than the Pfs25-AH-Pfs25 conjugate.

TABLE 2

Antibody production and transmission blocking activity of Pfs-25/NANP conjugates

| Antigen | Anti-CSP (EU/ml) | IFA (titer) | Anti-Pfs25 (EU/ml) | % oocyst reduction |
|---|---|---|---|---|
| (NANP)$_4$-tetanus toxoid | 64 | 160,000 | | |
| Pfs25-AH-Pfs25 | | | 136 | 94 |
| Pfs25-AH-Pfs25/(NANP)$_5$ | 98 | 640,000 | 96 | 42 |
| Pfs25-AH-Pfs25/(NANP)$_5$ + alum | 123 | 640,000 | 248 | 80 |
| Pfs25-AH-Pfs25/(NANP)$_5$ + alum (3 months later) | 409 | 4,000,000 | 784 | 100 |

EXAMPLE 3

Immunogenicity of CSP and NANP Conjugates

CSP and NANP conjugates were prepared as described in Example 1. 5-6 week-old NIH general purpose mice (n=10) were injected subcutaneously with 2.5 μg of NANP as conjugate 2 weeks apart. Mice were exsanguinated 7 days or 3 months after the second or third injection and IgG levels were measured. Serum IgG antibodies were measured by ELISA as described in Example 2. Conjugates included CSP conjugated to itself, CSP conjugated to Pfs25, (NANP)$_4$ conjugated to CSP, and NANP repeats with different end amino acids conjugated to BSA carrier protein.

All CSP conjugates were immunogenic in mice (Table 3). CSP repeats were also bound to different carrier proteins to test immunogenicity (Table 4). Anti-CSP levels increased with time (tested up to 3 months) when (NANP)$_5$ was bound to a Pfs25 conjugate. However, anti-CSP levels did not increase with time when (NANP)$_4$ was bound to BSA, and anti-CSP levels decreased over time when (NANP)$_4$ was bound to tetanus toxoid. (NPNA)$_5$ bound to Pfs25 conjugate did not generate anti-CSP antibodies, even when adsorbed on alum.

TABLE 3

Anti-CSP IgG levels in mice injected with CSP conjugates

| Preparation | Dose/mouse (μg) | IgG 2$^{nd}$ inj. | IgG 3$^{rd}$ inj. |
|---|---|---|---|
| CSP | 5 | 23 | 109 |
| CSP on formalin | 5 | | 47 |
| CSP on alum | 5 | 26 | 289 |
| CSP on formalin + alum | 5 | 39 | 137 |
| CSP-AH-CSP (1 step) | 2.5 | | 72 |

TABLE 3-continued

Anti-CSP IgG levels in mice injected with CSP conjugates

| Preparation | Dose/mouse (μg) | IgG 2nd inj. | IgG 3rd inj. |
|---|---|---|---|
| CSP-AH-CSP (2 step) | 2.5 | | 26 |
| CSP-AH-CSP (2 step) on alum | 2.5 | | 27 |
| Pfs25-AH-CSP F1 | 2.5 | | 39 |
| Pfs25-AH-CSP F2 | 2.5 | | 10 |
| (NANP)$_4$-CSP F1 | 2.5 | 30 | 216 |
| (NANP)$_4$-CSP F2 | 2.5 | 9 | 69 |

Anti-CSP expressed in EU/ml; NA = Not applicable

TABLE 4

Long term antibody response of CSP repeat peptides bound to different carrier proteins.

| Conjugate | No of chains per protein | Bleeding after last injection | IgG anti-CSP 2nd inj | IgG anti-CSP 3rd inj |
|---|---|---|---|---|
| (NANP)$_4$/BSA | 8 | 1 week | 16 | 152 |
|  | 8 | 3 months | 14 | 109 |
| (NANP)$_4$/TT | 30 | 1 week | — | 132 |
|  | 30 | 3 months | — | 22 |
| (NANP)$_5$/Pfs25-AH-Pfs25$_{alum\ ads.}$ | 5 | 1 week | 53 | — |
|  | 5 | 3 months | 120 | — |
| (NPNA)$_5$/Pfs-AH-Pfs | 3 | 1 week | 0.4 | 5 |
|  | 3 | 3 months | 0.3 | 18 |
| (NPNA)$_5$/PfS-AH-Pfs$_{alum\ ads.}$ | 3 | 1 week | 2 | 7 |
|  | 3 | 3 months | 3 | 13 | alum ads., adsorbed on alum

The NANP repeat variant and number of repeats conjugated to BSA influenced the immune response, with (NANP)$_5$ and (NPNA)$_5$ conjugates being the best immunogens (Table 5). In addition, the end amino acid appeared to influence immunogenicity, with conjugates ending in Asn generating the highest levels of anti-CSP antibodies. NANP repeat variants were also bound to Pfs25 conjugates and adsorbed on alum. The end amino acid affected immunogenicity, with NANP being the most immunogenic of the CSP repeat-Pfs25 conjugates (Table 6).

TABLE 5

Anti-CSP IgG levels in mice injected with NANP or variant repeat conjugates

| Conjugate | End Group | Mol. Mass (kDa) | Avg. No. of Chains/BSA | BSA: Repeat Ratio (wt/wt) | Exp. 1 (3rd inj.) Dose/Mouse (μg)* | Exp. 1 (3rd inj.) Anti-CSP IgG | Exp. 2 (3rd inj.) Dose/Mouse (μg)** | Exp. 2 (3rd inj.) Anti-CSP IgG |
|---|---|---|---|---|---|---|---|---|
| (ANPN)$_5$-BSA | Ala | 118 | 23 | 1:0.68 | 1.7 | 0.2 | 2.5 | 9 |
| (ANPN)$_5$-BSA | Ala | 97 | 12 | 1:0.35 | 1.6 | 6 | 2.5 | 6 |
| (ANPN)$_5$-BSA | Ala | 90 | 8 | 1:0.26 | ND | ND | 2.5 | 0.7 |
| (NANP)$_5$-BSA | Asn | 112 | 19 | 1:0.6 | 1.7 | 8 | 2.5 | 34 |
| (NANP)$_5$-BSA | Asn | 98 | 12 | 1:0.38 | 1.8 | 18 | 2.5 | 91 |
| (NANP)$_5$-BSA | Asn | 90 | 8 | 1:0.26 | ND | ND | 2.5 | 56 |
| (PNAN)$_5$-BSA | Pro | 118 | 23 | 1:0.68 | 1.5 | 0.1 | 2.5 | 5 |
| (PNAN)$_5$-BSA | Pro | 95 | 11 | 1:0.33 | 1.6 | 5 | 2.5 | 36 |
| (PNAN)$_5$-BSA | Pro | 90 | 8 | 1:0.26 | ND | ND | 2.5 | 7 |
| (NPNA)$_5$-BSA | Asn | 101 | 14 | 1:0.42 | 1.6 | 40 | 2.5 | 188 |
| (NPNA)$_5$-BSA | Asn | 90 | 8 | 1:0.26 | 1.2 | 42 | 2.5 | 117 |
| (NPNA)$_5$-BSA | Asn | 90 | 8 | 1:0.26 | ND | ND | 5.0 | 41 |

TABLE 5-continued

Anti-CSP IgG levels in mice injected with NANP or variant repeat conjugates

| Conjugate | End Group | Avg. Mol. Mass (kDa) | No. of Chains/BSA | BSA: Repeat Ratio (wt/wt) | Exp. 1 ($3^{rd}$ inj.) Dose/Mouse (μg)* | Exp. 1 ($3^{rd}$ inj.) Anti-CSP IgG | Exp. 2 ($3^{rd}$ inj.) Dose/Mouse (μg)** | Exp. 2 ($3^{rd}$ inj.) Anti-CSP IgG |
|---|---|---|---|---|---|---|---|---|
| $(NPNA)_5$-BSA | Asn | 90 | 8 | 1:0.26 | ND | ND | 1.25 | 28 |
| $(NPNA)_5$-BSA | Asn | 90 | 8 | 1:0.26 | ND | ND | 0.625 | 0.7 |

*Approximate amount of NANP (or other repeat) in the construct (actual concentration was not available at the time)
**Amount of NANP (or other repeat in the construct)

TABLE 6

Effect of terminal amino acid of CSP repeat bound to Pfs25 conjugate

| | | IgG [EU] | | | |
|---|---|---|---|---|---|
| | Av. no. of | anti-Pfs25 | | anti-CSP | |
| Conjugate | chains per Pfs25 | $2^{nd}$ inj. | $3^{rd}$ inj. | $2^{nd}$ inj. | $3^{rd}$ inj. |
| $ANPN_5$/Pfs25-AH-Pfs25$_{alum\,ad.}$ | 5 | — | 33 | — | 22 |
| $PNAN_5$/Pfs25-AH-Pfs25$_{alum\,ad.}$ | 5 | — | 4 | — | 17 |
| $NANP_5$/Pfs25-AH-Pfs25$_{alum\,ad.}$ | 4 | 6 | 180 | 7 | 110 |
| $NPNA_5$/Pfs25-AH-Pfs25$_{alum\,ad.}$ | 5 | 3 | 10 | 2 | 13 |

EXAMPLE 4

Immunogenicity of Malarial T-Cell Epitope/NANP Repeat Conjugates

A *Plasmodium falciparum* CSP universal T-cell epitope/$NANP_4$ repeat was conjugated with BSA as described in Example 1. Additional universal T-cell epitope/NANP repeat or variant sequences that can be conjugated with BSA are shown in Table 7. Similar conjugates are prepared with the CSP T cell epitope having the sequence $(DPNANPNV)_2$ (SEQ ID NO: 13).

TABLE 7

T-cell Epitope/NANP Repeat or Variant Peptides Conjugated to BSA

T-cell Epitope/NANP Repeat Peptide Sequences $(NANP)_4$-EYLNKIQNSLSTEWSPCSVT (SEQ ID NO: 25)

$(NANP)_5$-EYLNKIQNSLSTEWSPCSVT (SEQ ID NO: 26)

$(ANPN)_4$-EYLNKIQNSLSTEWSPCSVT (SEQ ID NO: 27)

$(ANPN)_5$-EYLNKIQNSLSTEWSPCSVT (SEQ ID NO: 28)

$(NPNA)_4$-EYLNKIQNSLSTEWSPCSVT (SEQ ID NO: 29)

$(NPNA)_5$-EYLNKIQNSLSTEWSPCSVT (SEQ ID NO: 30)

$(PNAN)_4$-EYLNKIQNSLSTEWSPCSVT (SEQ ID NO: 31)

$(PNAN)_5$-EYLNKIQNSLSTEWSPCSVT (SEQ ID NO: 32)

The CSP universal T-cell epitope/$NANP_4$ repeat conjugated with BSA was injected subcutaneously in 5-6 week old NIH general purpose mice 2 weeks apart. Mice were exsanguinated 7 days or 3 months after the second or third injection and IgG levels were measured by ELISA as described in Example 2.

The effect of including the T cell epitope in the $(NANP)_4$-BSA conjugate is shown in Table 8. The GM IgG anti-CSP levels induced by conjugates containing the T-cell epitope were lower (71 vs. 152) and the antibody levels declined faster than without the T-cell peptide (12 vs. 109, after 3 month) after 3 injections.

TABLE 8

Effect of T-cell epitope on long term immune response in mice

| Conjugate | No of chains per BSA | Protein conc. (mg/ml) | NANP conc. (mg/ml) | Bleeding after last injection | IgG anti-CSP $2^{nd}$ inj | IgG anti-CSP $3^{rd}$ inj |
|---|---|---|---|---|---|---|
| $NANP_4$/BSA | 8 | 3.5 | 0.5 | 1 week | 16 | 152 |
| | 8 | 3.5 | 0.5 | 3 months | 14 | 109 |
| $NANP_4$-Tcell/BSA | 6 | 0.78 | 0.093 | 1 week | 10 | 71 |
| | 6 | 0.78 | 0.093 | 3 months | 5 | 12 |

EXAMPLE 5

Safety and Efficacy of Candidate Vaccines in Human Subjects

The safety and efficacy of candidate malaria vaccines can be demonstrated in human volunteers according to procedures well known in the art. Typically, human volunteers are selected from those at risk of infection with malaria, such as residents of areas where malaria is endemic or travelers to those areas. All volunteers are screened to ensure they are in good health. Informed consent is obtained from each volunteer prior to vaccination.

In this example, human volunteers are injected with candidate vaccine subcutaneously or intramuscularly at an appropriate dose. The appropriate dose can be determined from suitable animal studies conducted prior to human vaccination trials. Other routes of administration are possible, including intramuscular and intravenous. The vaccine can be administered as a single dose, or given in multiple doses, such as two, three or four doses. When administered in multiple doses, the booster doses can be administered at various time intervals, such as months to years. Serum samples can be obtained to determine antibody titers and identify responders and non-responders to the vaccine.

Vaccinated volunteers are encouraged to return and report local or systemic reactions. Local reactions are assessed by grading pain and tenderness at the site of inoculation and/or axillary lymph nodes and measuring erythema and induration at the site. Systemic reaction parameters include fever, chills, headache, malaise, myalgia, arthralgia, sore throat, gastric upset, dizziness, photophobia and skin rash. Additional laboratory samples, including complete blood cell count, chemistry profile, urinalysis, and blood samples for detection of parasites can be obtained.

An immunogenic composition that is an effective vaccine candidate will result in production of antibodies to the proteins included in the compositions (such as *Plasmodium* sexual stage surface protein, CSP, or immunogenic portions thereof) and may also reduce or prevent the presence of parasites in inoculated volunteers as compared with mock-vaccinated controls.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. An immunogenic conjugate comprising:

a peptide comprising at least one repeat circumsporozoite protein selected from the group consisting of (NPNA)x, (PNAN)x, and (ANPN)x, wherein x is four to six;

covalently linked to at least one other immunogenic protein selected from the group consisting of bovine serum albumin, ovalbumin, tetanus toxoid, diphtheria toxoid, cholera toxin, *Clostridium difficile* toxin A, *Clostridium difficile* toxin B, and *Pseudomonas aeruginosa* recombinant exoprotein A, wherein the conjugate elicits an immune response to a *Plasmodium falciparum* circumsporozoite protein in a subject.

2. The immunogenic conjugate of claim 1, wherein the covalent linkage comprises a non-peptide linkage.

3. The immunogenic conjugate of claim 2, wherein the non-peptide linkage comprises at least one linkage selected from the group consisting of an amide linkage, a hydrazone linkage, a thioether linkage, and a combination of two or more thereof.

4. The immunogenic conjugate of claim 1, wherein the at least one repeat comprises $(NPNA)_4$ or $(NPNA)_5$.

5. The immunogenic conjugate of claim 1, wherein the at least one repeat comprises $(PNAN)_4$ or $(PNAN)_5$.

6. The immunogenic conjugate of claim 1, wherein the at least one repeat comprises $(ANPN)_4$ or $(ANPN)_5$.

7. A method of eliciting an immune response to a circumsporozoite protein of *Plasmodium falciparum* in a host, comprising administering the immunogenic conjugate of claim 1 to the host.

8. The method of claim 7, wherein the host is a human.

9. A pharmaceutical composition for eliciting an immune response to circumsporozoite protein of *Plasmodium falciparum* in a host, the composition comprising the immunogenic conjugate of claim 1 and a pharmaceutically acceptable carrier.

10. The pharmaceutical composition of claim 9, further comprising an adjuvant.

11. The pharmaceutical composition of claim 10, wherein the adjuvant is aluminum hydroxide.

12. A method of eliciting an immune response to a circumsporozoite protein of *Plasmodium falciparum* in a host, comprising administering the pharmaceutical composition of claim 9 to the host.

* * * * *

```
                         SEQUENCE LISTING

<160> NUMBER OF SEQ ID NOS: 32

<210> SEQ ID NO 1
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 1

Asn Ala Asn Pro
1

<210> SEQ ID NO 2
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 2

Asn Pro Asn Ala
1

<210> SEQ ID NO 3
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 3

Pro Asn Ala Asn
1

<210> SEQ ID NO 4
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 4

Ala Asn Pro Asn
```

<210> SEQ ID NO 5
<211> LENGTH: 982
<212> TYPE: DNA
<213> ORGANISM: Plasmodium falciparum

<400> SEQUENCE: 5

```
gagatatcct gttccaggaa tatcaatgct acggatccag cagcaacacg cgtgttctga    60
acgaactgaa ctacgataac gctggtacca atctgtacaa cgaactggaa atgaactact   120
acggtaaaca ggaaaactgg tacagcctga aaaaaaacag cagatctcta ggcgaaaacg   180
acgacggcaa caacaacaac ggtgataacg gtcgcgaagg taaagacgaa gacaaacgcg   240
acggcaacaa cgaagacaac gaaaaacttc gcaaaccgaa acacaaaaaa cttaagcagc   300
caggggatgg taatccagat ccgaacgcga atccgaacgt agacccgaac gcaaacccga   360
acgtagaccc gaacgcaaac ccgaacgtag acccgaacgc gaatccgaac gcgaacccta   420
acgcgaaccc gaacgcgaac ccgaacgcga acccgaacgc gaacccgaac gcgaacccga   480
acgcgaaccc gaacgcgaac ccgaacgcga acccgaacgc gaacccgaac gcgaacccga   540
acgcgaaccc gaacgcgaac ccgaacgcga acccgaacgc gaacccgaac gcgaacccga   600
acgcgaaccc gaacgcgaac ccgaacgcga acccgaacgc gaacccgaac aaaaacaatc   660
agggtaatgg ccagggtcac aatatgccaa atgacccaaa ccgaaatgta gatgaaaatg   720
ctaatgccaa caatgctgta aaaaataata ataacgaaga accaagtgat aagcacatag   780
aacaatattt aaagaaaata caaaattctc tttcaactga atggtcccca tgtagtgtaa   840
cttgcggcaa cggtattcag gtgcgcatca agccgggctc tgctaacaaa cctaaggacg   900
aactggatta cgaaaacgat atcgaaaaaa agatctgtaa gatggaacac catcatcatc   960
accattaatg agcggccgca ct                                            982
```

<210> SEQ ID NO 6
<211> LENGTH: 321
<212> TYPE: PRT
<213> ORGANISM: Plasmodium falciparum

<400> SEQUENCE: 6

```
Met Gly Leu Phe Gln Glu Tyr Gln Cys Tyr Gly Ser Ser Ser Asn Thr
  1               5                  10                  15

Arg Val Leu Asn Glu Leu Asn Tyr Asp Asn Ala Gly Thr Asn Leu Tyr
             20                  25                  30

Asn Glu Leu Glu Met Asn Tyr Tyr Gly Lys Gln Glu Asn Trp Tyr Ser
         35                  40                  45

Leu Lys Lys Asn Ser Arg Ser Leu Gly Glu Asn Asp Asp Gly Asn Asn
     50                  55                  60

Asn Asn Gly Asp Asn Gly Arg Glu Gly Lys Asp Glu Asp Lys Arg Asp
 65                  70                  75                  80

Gly Asn Asn Glu Asp Asn Glu Lys Leu Arg Lys Pro Lys His Lys Lys
                 85                  90                  95

Leu Lys Gln Pro Gly Asp Gly Asn Pro Asp Pro Asn Ala Asn Pro Asn
            100                 105                 110

Val Asp Pro Asn Ala Asn Pro Asn Val Asp Pro Asn Ala Asn Pro Asn
        115                 120                 125

Val Asp Pro Asn Ala Asn Pro Asn Ala Asn Pro Asn Ala Asn Pro Asn
    130                 135                 140
```

Ala Asn Pro Asn Ala Asn Pro Asn Ala Asn Pro Asn
145                 150                 155                 160

Ala Asn Pro Asn Ala Asn Pro Asn Ala Asn Pro Asn
                165                 170                 175

Ala Asn Pro Asn Ala Asn Pro Asn Ala Asn Pro Asn
            180                 185                 190

Ala Asn Pro Asn Ala Asn Pro Asn Ala Asn Pro Asn
        195                 200                 205

Ala Asn Pro Asn Ala Asn Pro Asn Lys Asn Asn Gln Gly Asn Gly Gln
    210                 215                 220

Gly His Asn Met Pro Asn Asp Pro Asn Arg Asn Val Asp Glu Asn Ala
225                 230                 235                 240

Asn Ala Asn Asn Ala Val Lys Asn Asn Asn Glu Glu Pro Ser Asp
                245                 250                 255

Lys His Ile Glu Gln Tyr Leu Lys Lys Ile Gln Asn Ser Leu Ser Thr
            260                 265                 270

Glu Trp Ser Pro Cys Ser Val Thr Cys Gly Asn Gly Ile Gln Val Arg
        275                 280                 285

Ile Lys Pro Gly Ser Ala Asn Lys Pro Lys Asp Glu Leu Asp Tyr Glu
    290                 295                 300

Asn Asp Ile Glu Lys Lys Ile Cys Lys Met Glu His His His His
305                 310                 315                 320

His

<210> SEQ ID NO 7
<211> LENGTH: 179
<212> TYPE: PRT
<213> ORGANISM: Plasmodium falciparum

<400> SEQUENCE: 7

Glu Ala Glu Ala Tyr Val Lys Val Thr Val Asp Thr Val Cys Lys Arg
1               5                   10                  15

Gly Phe Leu Ile Gln Met Ser Gly His Leu Glu Cys Lys Cys Glu Asn
                20                  25                  30

Asp Leu Val Leu Val Asn Glu Glu Thr Cys Glu Glu Lys Val Leu Lys
            35                  40                  45

Cys Asp Glu Lys Thr Val Asn Lys Pro Cys Gly Asp Phe Ser Lys Cys
50                  55                  60

Ile Lys Ile Asp Gly Asn Pro Val Ser Tyr Ala Cys Lys Cys Asn Leu
65                  70                  75                  80

Gly Tyr Asp Met Val Asn Asn Val Cys Ile Pro Asn Glu Cys Lys Gln
                85                  90                  95

Val Thr Cys Gly Asn Gly Lys Cys Ile Leu Asp Thr Ser Asn Pro Val
            100                 105                 110

Lys Thr Gly Val Cys Ser Cys Asn Ile Gly Lys Val Pro Asn Val Gln
        115                 120                 125

Asp Gln Asn Lys Cys Ser Arg Asp Gly Glu Thr Lys Cys Ser Leu Lys
    130                 135                 140

Cys Leu Lys Glu Gln Glu Thr Cys Lys Ala Val Asp Gly Ile Tyr Lys
145                 150                 155                 160

Cys Asp Cys Lys Asp Gly Phe Ile Ile Asp Gln Glu Ser Ser Ile Cys
                165                 170                 175

Thr Asp Pro

```
<210> SEQ ID NO 8
<211> LENGTH: 180
<212> TYPE: PRT
<213> ORGANISM: Plasmodium vivax

<400> SEQUENCE: 8

Glu Ala Glu Ala Ser Ala Val Thr Val Asp Thr Ile Cys Lys Asn Gly
1               5                   10                  15

Gln Leu Val Gln Met Ser Asn His Phe Lys Cys Met Cys Asn Glu Gly
            20                  25                  30

Leu Val His Leu Ser Glu Asn Thr Cys Glu Glu Lys Asn Glu Cys Lys
        35                  40                  45

Lys Glu Thr Leu Gly Lys Ala Cys Gly Glu Phe Gly Gln Cys Ile Glu
    50                  55                  60

Asn Pro Asp Pro Ala Gln Val Asn Met Tyr Lys Cys Gly Cys Ile Glu
65                  70                  75                  80

Gly Tyr Thr Leu Lys Glu Asp Thr Cys Val Leu Asp Val Cys Gln Tyr
                85                  90                  95

Lys Asn Cys Gly Glu Ser Gly Glu Cys Ile Val Glu Tyr Leu Ser Glu
            100                 105                 110

Ile Gln Ser Ala Gly Cys Ser Cys Ala Ile Gly Lys Val Pro Asn Pro
        115                 120                 125

Glu Asp Glu Lys Lys Cys Thr Lys Thr Gly Thr Ala Cys Gln Leu
    130                 135                 140

Lys Cys Asn Thr Asp Asn Glu Val Cys Lys Asn Val Glu Gly Val Tyr
145                 150                 155                 160

Lys Cys Gln Cys Met Glu Gly Phe Thr Phe Asp Lys Glu Lys Asn Val
                165                 170                 175

Cys Leu Gly Pro
            180

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is Asp or Ala

<400> SEQUENCE: 9

Xaa Gly Gln Pro Ala Gly Asp Arg Ala
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is Gly or Asp

<400> SEQUENCE: 10

Xaa Asn Gly Pro Gly Ala Asn Gly Ala
1               5

<210> SEQ ID NO 11
```

```
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 11

Asn Ala Ala Gly
1

<210> SEQ ID NO 12
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 12

Gln Ala Gln Gly Asp Gly Ala Asn Gly Gln Pro
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 13

Ala Pro Gly Ala Asn Gln Glu Gly Gly Ala Ala
1               5                   10

<210> SEQ ID NO 14
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 14

Glu Tyr Leu Asn Lys Ile Gln Asn Ser Leu Ser Thr Glu Trp Ser Pro
1               5                   10                  15

Cys Ser Val Thr
            20

<210> SEQ ID NO 15
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 15

Asp Pro Asn Ala Asn Pro Asn Val Asp Pro Asn Ala Asn Pro Asn Val
1               5                   10                  15

Asp Pro Asn Ala Asn Pro Asn Val Asp Pro Asn Ala Asn Pro Asn Val
            20                  25                  30

<210> SEQ ID NO 16
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 16
```

```
Asn Ala Asn Pro Asn Ala Asn Pro Asn Ala Asn Pro Asn Ala Asn Pro
1               5                   10                  15

<210> SEQ ID NO 17
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 17

Asn Ala Asn Pro Asn Ala Asn Pro Asn Ala Asn Pro Asn Ala Asn Pro
1               5                   10                  15

Asn Ala Asn Pro
            20

<210> SEQ ID NO 18
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 18

Asn Pro Asn Ala Asn Pro Asn Ala Asn Pro Asn Ala Asn Pro Asn Ala
1               5                   10                  15

<210> SEQ ID NO 19
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 19

Asn Pro Asn Ala Asn Pro Asn Ala Asn Pro Asn Ala Asn Pro Asn Ala
1               5                   10                  15

Asn Pro Asn Ala
            20

<210> SEQ ID NO 20
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 20

Pro Asn Ala Asn Pro Asn Ala Asn Pro Asn Ala Asn Pro Asn Ala Asn
1               5                   10                  15

<210> SEQ ID NO 21
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 21

Pro Asn Ala Asn Pro Asn Ala Asn Pro Asn Ala Asn Pro Asn Ala Asn
1               5                   10                  15

Pro Asn Ala Asn
            20

<210> SEQ ID NO 22
```

-continued

```
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 22

Ala Asn Pro Asn Ala Asn Pro Asn Ala Asn Pro Asn Ala Asn Pro Asn
1               5                   10                  15

<210> SEQ ID NO 23
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 23

Ala Asn Pro Asn Ala Asn Pro Asn Ala Asn Pro Asn Ala Asn Pro Asn
1               5                   10                  15

Ala Asn Pro Asn
            20

<210> SEQ ID NO 24
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 24

Asn Ala Asn Pro Asn Ala Asn Pro Asn Ala Asn Pro Asn Ala Asn Pro
1               5                   10                  15

Asn Ala Asn Pro Asn Ala Asn Pro
            20

<210> SEQ ID NO 25
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 25

Asn Ala Asn Pro Asn Ala Asn Pro Asn Ala Asn Pro Asn Ala Asn Pro
1               5                   10                  15

Glu Tyr Leu Asn Lys Ile Gln Asn Ser Leu Ser Thr Glu Trp Ser Pro
            20                  25                  30

Cys Ser Val Thr
        35

<210> SEQ ID NO 26
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 26

Asn Ala Asn Pro Asn Ala Asn Pro Asn Ala Asn Pro Asn Ala Asn Pro
1               5                   10                  15

Asn Ala Asn Pro Glu Tyr Leu Asn Lys Ile Gln Asn Ser Leu Ser Thr
            20                  25                  30

Glu Trp Ser Pro Cys Ser Val Thr
```

```
                35                  40

<210> SEQ ID NO 27
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 27

Ala Asn Pro Asn Ala Asn Pro Asn Ala Asn Pro Asn Ala Asn Pro Asn
1               5                   10                  15

Glu Tyr Leu Asn Lys Ile Gln Asn Ser Leu Ser Thr Glu Trp Ser Pro
            20                  25                  30

Cys Ser Val Thr
        35

<210> SEQ ID NO 28
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 28

Ala Asn Pro Asn Ala Asn Pro Asn Ala Asn Pro Asn Ala Asn Pro Asn
1               5                   10                  15

Ala Asn Pro Asn Glu Tyr Leu Asn Lys Ile Gln Asn Ser Leu Ser Thr
            20                  25                  30

Glu Trp Ser Pro Cys Ser Val Thr
        35                  40

<210> SEQ ID NO 29
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 29

Asn Pro Asn Ala Asn Pro Asn Ala Asn Pro Asn Ala Asn Pro Asn Ala
1               5                   10                  15

Glu Tyr Leu Asn Lys Ile Gln Asn Ser Leu Ser Thr Glu Trp Ser Pro
            20                  25                  30

Cys Ser Val Thr
        35

<210> SEQ ID NO 30
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 30

Asn Pro Asn Ala Asn Pro Asn Ala Asn Pro Asn Ala Asn Pro Asn Ala
1               5                   10                  15

Asn Pro Asn Ala Glu Tyr Leu Asn Lys Ile Gln Asn Ser Leu Ser Thr
            20                  25                  30

Glu Trp Ser Pro Cys Ser Val Thr
        35                  40
```

-continued

```
<210> SEQ ID NO 31
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 31

Pro Asn Ala Asn Pro Asn Ala Asn Pro Asn Ala Asn Pro Asn Ala Asn
1               5                   10                  15

Glu Tyr Leu Asn Lys Ile Gln Asn Ser Leu Ser Thr Glu Trp Ser Pro
            20                  25                  30

Cys Ser Val Thr
        35

<210> SEQ ID NO 32
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 32

Pro Asn Ala Asn Pro Asn Ala Asn Pro Asn Ala Asn Pro Asn Ala Asn
1               5                   10                  15

Pro Asn Ala Asn Glu Tyr Leu Asn Lys Ile Gln Asn Ser Leu Ser Thr
            20                  25                  30

Glu Trp Ser Pro Cys Ser Val Thr
        35                  40
```